US009550053B2

(12) United States Patent
Ross

(10) Patent No.: US 9,550,053 B2
(45) Date of Patent: Jan. 24, 2017

(54) TRANSDERMAL DELIVERY OF HIGH VISCOSITY BIOACTIVE AGENTS

(71) Applicant: Kimberly-Clark Worldwide, Inc., Neenah, WI (US)

(72) Inventor: Russell F. Ross, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 4 days.

(21) Appl. No.: 14/354,229

(22) PCT Filed: Oct. 16, 2012

(86) PCT No.: PCT/IB2012/055621
§ 371 (c)(1),
(2) Date: Apr. 25, 2014

(87) PCT Pub. No.: WO2013/061208
PCT Pub. Date: May 2, 2013

(65) Prior Publication Data
US 2014/0343532 A1 Nov. 20, 2014

Related U.S. Application Data

(60) Provisional application No. 61/552,069, filed on Oct. 27, 2011.

(51) Int. Cl.
*A61M 5/32* (2006.01)
*A61M 37/00* (2006.01)
*A61K 9/00* (2006.01)

(52) U.S. Cl.
CPC ........ *A61M 37/0015* (2013.01); *A61K 9/0021* (2013.01); *A61M 2037/003* (2013.01);
(Continued)

(58) Field of Classification Search
CPC ................ A61M 37/0015; A61M 2037/0007; A61M 2037/0023; A61M 2037/0046; A61M 2037/0053; A61M 2037/0061; A61K 9/0021
See application file for complete search history.

(56) References Cited

U.S. PATENT DOCUMENTS 4,051,840 A 10/1977 Kantrowitz et al.
4,698,062 A 10/1987 Gale et al.
(Continued)

FOREIGN PATENT DOCUMENTS

EP 2 100 850 9/2009
EP 2100850 A1 9/2009
(Continued)

OTHER PUBLICATIONS

Biggs et al., "Interactions with nanoscale topography: Adhesion quantification and signal transduction in cells of osteogenic and multipotent lineage," *Journal of Biomedical Materials Research Part A*, 2008 Wiley, Periodicals, Inc., pp. 195-208.
(Continued)

*Primary Examiner* — Rebecca E Eisenberg
(74) *Attorney, Agent, or Firm* — Dority & Manning, P.A.

(57) ABSTRACT

A device and method for delivering a high viscosity composition is described. The composition includes a bioactive agent for delivery to a subject in need thereof. The method delivers the bioactive agent at a high bioavailability and with little loss of agent to the natural defense mechanisms of the body. The device includes one or more microneedles with structures fabricated on a surface of the microneedles to form a nanotopography. A random or non-random pattern of structures may be fabricated such as a complex pattern including structures of differing sizes and/or shapes.

41 Claims, 21 Drawing Sheets

(52) U.S. Cl.
CPC .............. *A61M 2037/0007* (2013.01); *A61M 2037/0023* (2013.01); *A61M 2037/0038* (2013.01); *A61M 2037/0046* (2013.01); *A61M 2037/0053* (2013.01); *A61M 2037/0061* (2013.01)

(56) References Cited

U.S. PATENT DOCUMENTS

| | | |
|---|---|---|
| 4,880,633 A | 11/1989 | Loper et al. |
| 5,310,559 A | 5/1994 | Shah et al. |
| 6,132,755 A | 10/2000 | Eicher et al. |
| 6,312,612 B1 | 11/2001 | Sherman et al. |
| 6,334,856 B1 | 1/2002 | Allen et al. |
| 6,375,978 B1 | 4/2002 | Kleiner et al. |
| 6,471,993 B1 | 10/2002 | Shastri et al. |
| 6,569,143 B2 | 5/2003 | Alchas et al. |
| 6,591,124 B2 | 7/2003 | Sherman et al. |
| 6,611,707 B1 | 8/2003 | Prausnitz et al. |
| 6,656,147 B1 | 12/2003 | Gertsek et al. |
| 6,663,820 B2 | 12/2003 | Arias et al. |
| 6,767,341 B2 | 7/2004 | Cho |
| 6,881,203 B2 | 4/2005 | Delmore et al. |
| 6,908,453 B2 | 6/2005 | Fleming et al. |
| 6,979,347 B1 | 12/2005 | Wu et al. |
| 6,995,336 B2 | 2/2006 | Hunt et al. |
| 7,048,723 B1 | 5/2006 | Frazier et al. |
| 7,066,922 B2 | 6/2006 | Angel et al. |
| 7,108,681 B2 | 9/2006 | Gartstein et al. |
| 7,115,108 B2 | 10/2006 | Wilkinson et al. |
| 7,129,554 B2 | 10/2006 | Lieber et al. |
| 7,131,987 B2 | 11/2006 | Sherman et al. |
| 7,185,663 B2 | 3/2007 | Koch et al. |
| 7,285,113 B2 | 10/2007 | Yeshurun |
| 7,315,758 B2 | 1/2008 | Kwiatkowski et al. |
| 7,332,339 B2 | 2/2008 | Canham |
| 7,374,864 B2 | 5/2008 | Guo et al. |
| 7,416,541 B2 | 8/2008 | Yuzhakov et al. |
| 7,473,244 B2 | 1/2009 | Frazier et al. |
| 7,531,120 B2 | 5/2009 | Van Rijn et al. |
| 7,537,590 B2 | 5/2009 | Santini, Jr. et al. |
| 7,556,615 B2 | 7/2009 | Pettis et al. |
| 7,572,405 B2 | 8/2009 | Sherman et al. |
| 7,578,954 B2 | 8/2009 | Gartstein et al. |
| 7,582,069 B2 | 9/2009 | Laurent et al. |
| 7,588,552 B2 | 9/2009 | Yeshurun |
| 7,611,481 B2 | 11/2009 | Cleary et al. |
| 7,627,938 B2 | 12/2009 | Kim et al. |
| 7,658,728 B2 | 2/2010 | Yuzhakov |
| 7,753,888 B2 | 7/2010 | Mukerjee et al. |
| 7,785,301 B2 | 8/2010 | Yuzhakov |
| 7,803,574 B2 | 9/2010 | Desai et al. |
| 7,828,827 B2 | 11/2010 | Gartstein et al. |
| 7,846,488 B2 | 12/2010 | Johnson et al. |
| 7,901,387 B2 | 3/2011 | Stemme et al. |
| 7,914,813 B2 | 3/2011 | Adachi et al. |
| 7,918,814 B2 | 4/2011 | Prausnitz et al. |
| 7,972,616 B2 | 7/2011 | Dubrow et al. |
| 7,981,346 B2 | 7/2011 | Griss et al. |
| 7,997,274 B2 | 8/2011 | Baska |
| 8,052,633 B2 | 11/2011 | Kendall |
| 8,057,842 B2 | 11/2011 | Choi et al. |
| 8,088,321 B2 | 1/2012 | Ferguson et al. |
| 8,097,456 B2 | 1/2012 | Borenstein et al. |
| 8,118,753 B2 | 2/2012 | Cho et al. |
| 8,137,736 B2 | 3/2012 | Zhu et al. |
| 8,162,901 B2 | 4/2012 | Gonnelli et al. |
| 8,238,995 B2 | 8/2012 | Chandrasekaran et al. |
| 8,366,677 B2 | 2/2013 | Kaspar et al. |
| 8,389,205 B2 | 3/2013 | Duerig et al. |
| 8,419,708 B2 | 4/2013 | Tokumoto et al. |
| 8,506,530 B2 | 8/2013 | Laermer et al. |
| 8,574,615 B2 | 11/2013 | Tenney et al. |
| 8,690,838 B2 | 4/2014 | Ozawa et al. |
| 8,696,637 B2 | 4/2014 | Ross |
| 8,747,886 B2 | 6/2014 | Amsden et al. |
| 8,915,957 B2 | 12/2014 | Arney et al. |
| 8,944,804 B2 | 2/2015 | Robeson et al. |
| 9,028,409 B2 | 5/2015 | Yodfat et al. |
| 9,050,444 B2 | 6/2015 | Gharib et al. |
| 9,314,548 B2 | 4/2016 | Robeson et al. |
| 2002/0082543 A1 | 6/2002 | Park et al. |
| 2002/0133129 A1 | 9/2002 | Arias et al. |
| 2002/0183688 A1 | 12/2002 | Lastovich et al. |
| 2003/0045837 A1 | 3/2003 | Delmore et al. |
| 2004/0028875 A1 | 2/2004 | Van Rijn et al. |
| 2004/0063100 A1 | 4/2004 | Wang |
| 2004/0087992 A1 | 5/2004 | Gartstein et al. |
| 2004/0176732 A1 | 9/2004 | Frazier et al. |
| 2005/0049625 A1 | 3/2005 | Shaya et al. |
| 2005/0112135 A1 | 5/2005 | Cormier et al. |
| 2005/0118388 A1 | 6/2005 | Kingsford |
| 2005/0119723 A1 | 6/2005 | Peacock, III |
| 2005/0124967 A1 | 6/2005 | Kaestner et al. |
| 2005/0137531 A1 | 6/2005 | Prausnitz et al. |
| 2005/0178760 A1 | 8/2005 | Chang et al. |
| 2005/0203613 A1 | 9/2005 | Arney et al. |
| 2006/0024358 A1 | 2/2006 | Santini, Jr. et al. |
| 2006/0025848 A1 | 2/2006 | Weber et al. |
| 2006/0051404 A1 | 3/2006 | Yeshurun et al. |
| 2006/0204738 A1 | 9/2006 | Dubrow et al. |
| 2006/0264893 A1 | 11/2006 | Sage, Jr. et al. |
| 2007/0066934 A1 | 3/2007 | Etheredge, III et al. |
| 2007/0078376 A1 | 4/2007 | Smith |
| 2007/0081977 A1 | 4/2007 | Horstmann |
| 2007/0088248 A1 | 4/2007 | Glenn et al. |
| 2007/0110810 A1 | 5/2007 | Smith |
| 2007/0112309 A1 | 5/2007 | Zucker |
| 2007/0112548 A1 | 5/2007 | Dickerson et al. |
| 2007/0191761 A1 | 8/2007 | Boone et al. |
| 2007/0249552 A1 | 10/2007 | Khalili et al. |
| 2007/0250018 A1 | 10/2007 | Adachi et al. |
| 2007/0276318 A1 | 11/2007 | Henley |
| 2007/0282247 A1 | 12/2007 | Desai et al. |
| 2008/0091226 A1 | 4/2008 | Yeshurun et al. |
| 2008/0097352 A1 | 4/2008 | Beck et al. |
| 2008/0108958 A1 | 5/2008 | Carter et al. |
| 2008/0167601 A1 | 7/2008 | Laermer et al. |
| 2008/0195035 A1 | 8/2008 | Frederickson et al. |
| 2008/0200883 A1 | 8/2008 | Tomono |
| 2008/0208076 A1 | 8/2008 | Cho et al. |
| 2008/0217180 A1 | 9/2008 | Doye et al. |
| 2008/0221408 A1 | 9/2008 | Hoarau et al. |
| 2008/0262416 A1 | 10/2008 | Duan et al. |
| 2008/0269666 A1 | 10/2008 | Wang et al. |
| 2008/0269685 A1 | 10/2008 | Singh et al. |
| 2008/0305989 A1 | 12/2008 | Wen et al. |
| 2008/0311172 A1 | 12/2008 | Schapira et al. |
| 2008/0312610 A1 | 12/2008 | Binks et al. |
| 2009/0012494 A1 | 1/2009 | Yeshurun et al. |
| 2009/0043279 A1 | 2/2009 | Kaspar et al. |
| 2009/0069788 A1 | 3/2009 | Yeshurun et al. |
| 2009/0093776 A1 | 4/2009 | Yue et al. |
| 2009/0093871 A1 | 4/2009 | Rea et al. |
| 2009/0093879 A1 | 4/2009 | Wawro et al. |
| 2009/0099502 A1 | 4/2009 | Tokumoto et al. |
| 2009/0099537 A1 | 4/2009 | DeVoe et al. |
| 2009/0118662 A1 | 5/2009 | Schnall |
| 2009/0137926 A1 | 5/2009 | Srinivasan et al. |
| 2009/0177273 A1 | 7/2009 | Piveteau et al. |
| 2009/0187167 A1 | 7/2009 | Sexton et al. |
| 2009/0198189 A1 | 8/2009 | Simons et al. |
| 2009/0232870 A1 | 9/2009 | Srivastava et al. |
| 2010/0004733 A1 | 1/2010 | Atanasoska et al. |
| 2010/0021464 A1 | 1/2010 | Archambeau et al. |
| 2010/0076035 A1 | 3/2010 | Carter et al. |
| 2010/0121307 A1 | 5/2010 | Lockard et al. |
| 2010/0168506 A1 | 7/2010 | Moon et al. |
| 2010/0215580 A1 | 8/2010 | Hanes et al. |
| 2010/0256568 A1 | 10/2010 | Frederickson et al. |
| 2010/0274203 A1 | 10/2010 | Lee et al. |
| 2010/0316960 A1 | 12/2010 | Duerig et al. |
| 2011/0021996 A1 | 1/2011 | Lee et al. |
| 2011/0046557 A1 | 2/2011 | Lee et al. |
| 2011/0144591 A1 | 6/2011 | Ross et al. |

(56) References Cited

U.S. PATENT DOCUMENTS

| | | |
|---|---|---|
| 2011/0270221 A1 | 11/2011 | Ross |
| 2011/0276003 A1 | 11/2011 | Luttge et al. |
| 2012/0089117 A1 | 4/2012 | Junginger et al. |
| 2012/0109065 A1 | 5/2012 | Backes |
| 2012/0114734 A1 | 5/2012 | Desai et al. |
| 2012/0128932 A1 | 5/2012 | Veith et al. |
| 2013/0144257 A1 | 6/2013 | Ross |
| 2013/0211310 A1 | 8/2013 | Bommarito et al. |
| 2013/0331792 A1 | 12/2013 | Karp et al. |
| 2014/0112921 A1 | 4/2014 | Ross |
| 2014/0287019 A1 | 9/2014 | Ollerenshaw et al. |
| 2014/0343532 A1 | 11/2014 | Ross |

FOREIGN PATENT DOCUMENTS

| | | |
|---|---|---|
| WO | WO 99/45860 | 9/1999 |
| WO | WO 01/75164 A2 | 10/2001 |
| WO | WO 02/30506 | 4/2002 |
| WO | WO 02/30506 A2 | 4/2002 |
| WO | WO 02/32480 A2 | 4/2002 |
| WO | WO 03/020359 A2 | 3/2003 |
| WO | WO 03/024508 A2 | 3/2003 |
| WO | WO 03/059431 | 7/2003 |
| WO | WO 2005/049128 | 6/2005 |
| WO | WO 2005/049128 A1 | 6/2005 |
| WO | WO 2006/062974 | 6/2006 |
| WO | WO 2006/062974 A2 | 6/2006 |
| WO | WO 2006/075689 A1 | 7/2006 |
| WO | WO 2007/012114 A1 | 2/2007 |
| WO | WO 2007012114 A1 | 2/2007 |
| WO | WO 2007/081876 | 7/2007 |
| WO | WO 2007081876 A2 | 7/2007 |
| WO | WO 2007081876 A3 | 7/2007 |
| WO | WO 2007/112309 A2 | 10/2007 |
| WO | WO 2008/003564 | 1/2008 |
| WO | WO 2008/003564 A1 | 1/2008 |
| WO | WO 2008/024141 | 2/2008 |
| WO | WO 2008/024141 A2 | 2/2008 |
| WO | WO 2008115883 A1 | 9/2008 |
| WO | WO 2009/049243 | 4/2009 |
| WO | WO 2009/079589 | 6/2009 |
| WO | WO 2009/079589 A2 | 6/2009 |
| WO | WO 2009/079712 | 7/2009 |
| WO | WO 2009/113856 | 9/2009 |
| WO | WO 2010/062919 | 6/2010 |
| WO | WO 2010/070628 A1 | 6/2010 |
| WO | WO 2010/126640 A2 | 11/2010 |
| WO | WO 2011/116388 A1 | 9/2011 |
| WO | WO 2011/135531 | 11/2011 |
| WO | WO 2011/135531 A2 | 11/2011 |
| WO | WO 2012/006677 | 1/2012 |
| WO | WO 2012/046149 A1 | 4/2012 |

OTHER PUBLICATIONS

International Search Report and Written Opinion for PCT/IB2012/055621 dated Feb. 28, 2013, 12 pages.
Abstract of Japanese Patent—JP2008237673, Oct. 9, 2008, 1 page.
Abstract of Japanese Patent—JP2009207733, Sep. 17, 2009, 1 page.
Abstract of Japanese Patent—JPH08337521, Dec. 24, 1996, 2 pages.
Inkyu Park et al., Towards the silicon nanowire-based sensor for intracellular biochemical detection, 6 pages, Apr. 1, 2007, Biosensors and Bioelectronics, vol. 22, No. 9-10.
Supplementary European Search Report dated Apr. 2, 2015, 8 pages.
Abstract of Japanese Patent—JP2001238964, Sep. 4, 2001, 1 page.
Ainslie et al., "Microfabricated Devices for Enhanced Bioadhesive Drug Delivery: Attachment to and Small-Molecule Release Through a Cell Monolayer Under Flow." Small. (2009).
Ainslie et al., "Microfabricated implants for applications in therapeutic delivery, tissue engineering, and biosensing." Royal Society of Chemistry. 8. (2008): 1864-1878.

Al-Qallaf et al., "Optimizing Microneedle Arrays to Increase Skin Permeability for Transdermal Drug Delivery," Interdisciplinary Transport Phenomena V: Ann. N.Y. Acad. Sci., 2009, pp. 1-12.
Bekarde, Iil Gercel. "Biomimetic Apatite-coated PCL Scaffolds: Effects of Surface Nanotopography on Cellular Functions." Journal of Bioactive and Compatible Polymers. 24.6 (2009): 507-524.
Berliner et al., "Impact of Transdermal Fentanyl on Quality of Life in Rheumatoid Arthritis", Clinical Journal of Pain, 2007, 23(6): 530-534.
Berry et al., "The interaction of human bone marrow cells with nanotopographical features in three dimensional constructs." Journal of Biomedical Materials Research Part A. 79A.2 (2006): 431-439.
Biehl et al., "Proliferation of Mouse Embryonic Stem Cell Progeny and the Spontaneous Contractile Activity of Cardiomyocytes Are Affected by Microtopography." Developmental Dynamics. 238. (2009): 1964-1973.
Chandler, David L., "PhysOrg.com." Harnessing nanopatterns: Tiny textures can produce big differences. N.p., Sep. 24, 2009. Web. Dec. 1, 2009. <http://www.physorg.com/news173004362.html>.
Choi et al. "Cell interaction with three-dimensional sharp-tip nanotopography." Biomaterials. 28.9 (2007): 1672-1679.
Chun et al., "The role of polymer nanosurcase roughness and the submicron pores in improving bladder urothelial cell density and inhibiting calcium oxalata stone formulation." Nanotechnology. 20.8 (2009): 85104.
Citi, S., "Protein Kinase Inhibitors Prevent Junction Dissociation Induced by Low Extracellular Calcium in MDCK Epithelial Cells", J Cell Biology, 1992, 117(1) 169-178.
Cohn, Abby. "Drug Delivery, Nanoscale." Innovations. 3.4 (2009).
Curtis et al., "Cell signaling arising from nanotopography: implicatinos for nanomedicaldevices." Nanomedicine. 1.1 (2006): 67-72.
Dalby et al., "Attempted endocytosis of nano-environment produced by colloidal lithography by human fibroblasts." Experimental Cell Research. 295. (2004): 387-394.
Dalby et al., "Increasing Fibroblast Response to Materials Using Nanotopography: Morphological and Genetic measurements of Cell Response to 13-nm-High Polymer Demixed Islands." Experimental Cell Research. 276.1 (2002): 1-9.
Dalby et al., "Nano-Topography Induces Mechanotransduction in Human Fibroblasts." European Cells and Materials. 6.2 (2003): 31.
Dalby, Matthew J. "Nanostructured surfaces: cell engineering and cell biology." European Cells and Materials. 6.2 (2003): 31.
Fischer et al., "Biomimetic Nanowire Coatings for Next Generation Adhesive Drug Delivery Systems." Nano Letters. 9.2 (2009): 716-720.
Hart et al., "Filapodial Sensing of Nanotopography in Osteoprogenitor Cells." European Cells and Materials. 10.2 (2005): 65.
He, et al., "The anatase phase of nanotopography titania plays an important role on osteoblast cell morphology and proliferation", Journal of Mater. Sci: Mater Med (2008), 19:3465-3472.
Hu et al., "Surface Energy Induced Patterning of Polymer Nanostructures for Cancer Diagnosis and Therapy." IEEE Nano 2007 Conference Paper. (2007).
Kumar et al. "Transdermal Drug Delivery System: An Overview." International Journal of Pharmaceutical Sciences Review and Research. 3.2 (2010): 49-54.
Lim et al., "Human foetal osteoblastic cell response to polymer-demixed nanotopographic interfaces." Journal of the Royal Society Interface. 2.2 (2005): 97-108.
Madara, JL, "Regulation of the movement of solutes across tight junctions", Annu Rev Physiol, 1998, 60:143-59.
Mahdavi et al., "A biodegradable and biocompatible gecko-inspired tissue adhesive." PNAS. 105.7 (2008): 2307-2312.
Martinez-Palomo et al., "Experimental Modulation of Occluding Junctions in a Cultured Transporting Epithelium", J. Cell Biology, 1980, 87: 736-745.
Meirelles et al., "The effect of chemical and nanotopographical modifications on the early stages of osseointegration." International Journal of Oral and Maxillofacial Implants. 23.4 (2008): 641-647.

(56) References Cited

OTHER PUBLICATIONS

Mendelsohn et al., "Inorganic Nanoporous Membrans for Immunoisolated Cell-Based Drug Delivery." Therapeutic Applications of Cell Microencapsulation.

Ng et al., "Study of substrate topographical effects on epithelial cell behavior using etched alpha-particle tracks on PADC films." Nuclear Instruments and Methods in Physics Research Section B: Beam Interactions with Materials and Atoms. 266.14 (2008): 3247-3256.

Ojakian, GK, "Tumor promotor-induced changes in the permeability of epithelial cell tight junctions", Cell, 1981, 23(1): 95-103.

Orr et al., "Submicrometer and Nanoscale Inorganic Particles Exploit the Actin Machinery to Be Propelled along Microvilli-likestructures into Alveolar Cells." American Chemical Society NANO. 1.5 (2007): 463-475.

Ozawa et al., "The cytoplasmic domain of the cell adhesion molecule uvomorulin associates with three independent proteins structurally related in different species", EMBO Journal, 1989, 8(6): 1711-1717.

Rubin, LL, "Endothelial cells: adhesion and tight junctions", Curr Opin Cell Biol, 1992, 4(5):830-3.

Rutten et al., "Electrical resistance and macromolecular permeability of brain endothelial monolayer cultures", Brain Res, 1987, 425(2):301-10.

Sapra et al., "Effect of Asparagus racemous Extract on Transdermal Delivery of Carvedilol: A Mechanistic Study." American Association of Pharmaceutical Scientists PharmSciTech. 10.1 (2009): 199.

Sapra et al., "Transdermal Delivery of Carvedilol Containing Glycyrrhizin and Chitosan as Permeation Enhancers:Biochemical, Biophysical, Microscopic and Pharmacodynamic Evaluation." Drug Delivery. 15.7 (2008): 443-454.

Sapra et al., "Transdermal delivery of carvedilol in rats: probing the percutaneous permeation enhancement mechanism of soybean extract-chitosan mixture." Drug Delivery. 35.10 (2009): 1230-1241.

Schubert et al, "Sliding-induced adhesion of stiff polymer microfibre arrays. II. Microscale behavior", J Royal Society; Jan. 2008, 5, 845-853.

Teo et al. "The effect of micro and nanotopography on endocytosis in drug and gene delivery systems", Biomaterials, 32 (2011), 9866-9875.

Thakar et al., "Contracility-Dependent Modulation of Cell Proliferation and Adhesion by Microscale Topographical Cues." Small. 4.9 (2008): 1416-1424.

Valenta et al., "The use of polymers for dermal and transdermal delivery." European Journal of Pharmaceuticals and Biopharmaceutics. 58.2 (2004): 279-289.

Verma et al., "Development of Transdermal Drug Dosage Formulation for the Anti-Rheumatic Ayurvedic Medicianal Plants", Ancient Sci. Life, 2007; 11:66-9.

Wang et al., "Nano patterned PDMS for periodontal ligament fibroblast culture." Surface and Coatings Technology. 204.4 (2009): 525-530.

Wei et al., "Protein adsorption on materials surfaces with nanotopography." Chinese Science Bulletin. 52.23 (2007): 3169-3173.

Wood, M.A. "Colloidal lithography and current fabrication techniques producing in-plane nanotopography for biological applications." Journal of the Royal Society Interface. 4.12 (2007): 1-17.

Yao et al., "Nano-Surface Modification on Titanium Implants for Drug Delivery." Materials Research Society. (2007).

Yim et al., "Nanopattern-induced changes in morphology and motility of smooth muscle cells." Journal of Biomaterials. 58.1 (2005).

*square packing*       *hexagonal packing*

DN1

Hole depth = 500nm

DN2

Hole depth = 500nm

DN3

Hole Depth = 500 nm

DN4

Hole depth = 400-550nm (Random Variation)

FIG. 24E
NTTAT2
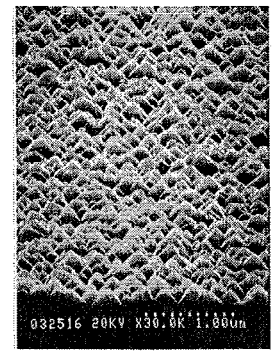
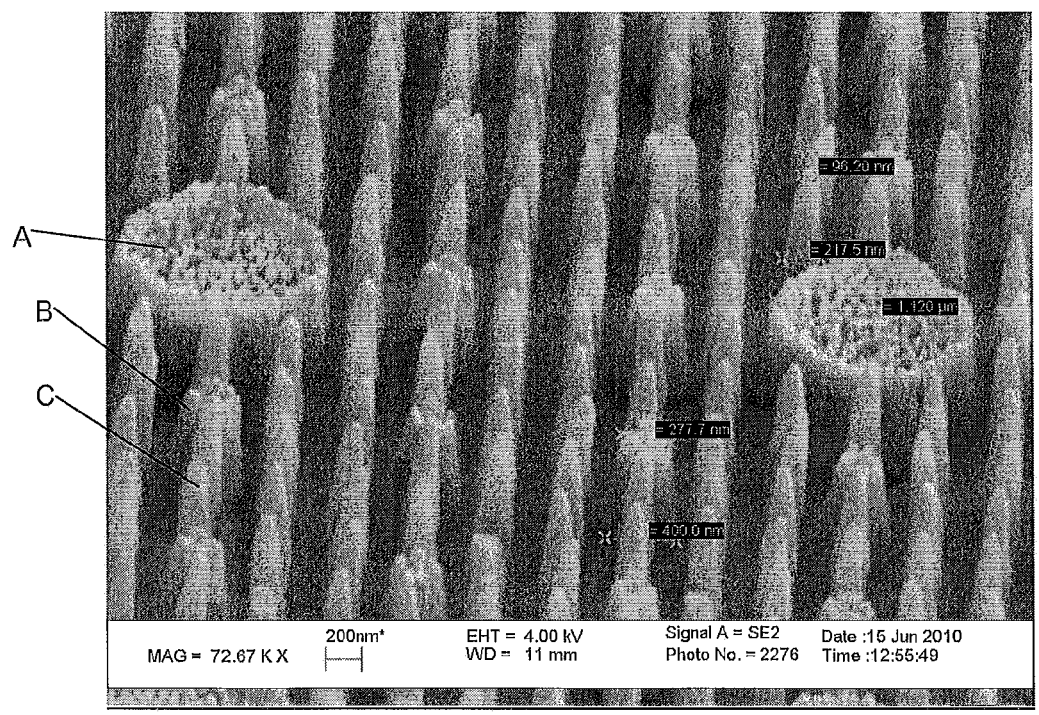
FIG. 25

TRANSDERMAL DELIVERY OF HIGH VISCOSITY BIOACTIVE AGENTS

CROSS REFERENCE TO RELATED APPLICATIONS

The present application is the U.S. national filing of International Patent Application Number PCT/IB2012/055621 having a filing date of Oct. 16, 2012, which claims filing benefit of U.S. Provisional Patent Application Ser. No. 61/552,069 having a filing date of Oct. 27, 2011, both of which are incorporated herein by reference in their entirety.

BACKGROUND

Targeted drug delivery in which a bioactive agent (e.g., a drug or a therapeutic) is provided in an active state to a subject's system at effective concentrations is a long sought goal. Many difficulties must be overcome to reach this goal. For instance, a bioactive agent must first be successfully delivered internally, and the human body has developed many barriers to prevent the influx of foreign substances. In addition, the nature of the bioactive agent itself or the concentration of a bioactive agent necessary to obtain the desired effect often leads to formation of a high viscosity composition, which further amplifies the difficulties in successfully passing the body's natural barriers.

Delivery methods presently utilized for high viscosity compositions include oral delivery, injections, and infusions. Unfortunately, these methods all include aspects that are problematic not only with regard to successful delivery of the high viscosity composition, but also for the subject receiving the composition. For instance, injections often utilize small gauge needles that require extremely high pressure over a long period of time for delivery of high viscosity compositions, if they are capable of use for the high viscosity compositions at all. For example, 0.5 milliliter of a 20 centipoise (cP) proteinaceous solution can take up to about 600 seconds for delivery through a 34 gauge needle. In addition, injections are painful particularly when considering the time required for a single dose delivery and, when considering long term use of an agent, can lead to development of scar tissue. Oral delivery requires successful absorption through the epithelial lining of the digestive tract as well as avoidance of break down of the bioactive agent by digestive materials, and both of these hurdles can be extremely difficult to cross. In addition, oral delivery often leads to gastrointestinal distress for the subject. Moreover, both injection and oral delivery tend to provide bursts of agents and wide swings in system concentration rather than a preferred steady-state delivery. Infusion therapy can be used to deliver bioactive agents directly to blood vessels, muscles, or subcutaneous connective tissue. While delivery via infusion therapy now can be carried out on an out-patient basis, or even with long term, relatively steady-state delivery by use of infusion pumps, infusion therapy is invasive, increasing chances for infection at the infusion site, and necessitates the utilization of associated equipment such as pumps, transdermal tubing, etc.

Transdermal delivery devices have been developed in an attempt to provide a painless route for successful delivery of bioactive agents over a sustained period. For instance, transdermal delivery patches have been found useful for providing bioactive agents such as nicotine, scopolamine, estrogen, nitroglycerine, and the like to a subject's system. In order to be successful, a transdermal scheme must deliver an agent across the epidermis, which has evolved with a primary function of keeping foreign substances out. The outermost layer of the epidermis, the stratum corneum, has structural stability provided by overlapping corneocytes and crosslinked keratin fibers held together by coreodesmosomes and embedded within a lipid matrix, all of which provides an excellent barrier function. Beneath the stratum corneum is the stratum granulosum, within which tight junctions are formed between keratinocytes. Tight junctions are barrier structures that include a network of transmembrane proteins embedded in adjacent plasma membranes (e.g., claudins, occludin, and junctional adhesion molecules) as well as multiple plaque proteins (e.g., ZO-1, ZO-2, ZO-3, cingulin, symplekin). Tight junctions are found in internal epithelium and endothelium (e.g., the intestinal epithelium, the blood-brain barrier, blood vessel walls) as well as in the stratum granulosum of the skin. Beneath both the stratum corneum and the stratum granulosum lays the stratum spinosum. The stratum spinosum includes Langerhans cells, which are dendritic cells that may become fully functioning antigen-presenting cells and may institute an immune response and/or a foreign body response to an invading agent.

The addition of microneedles on transdermal delivery devices such as patches has helped to breach initial barriers in the dermis. Unfortunately, even with such improvements, transdermal delivery devices are presently limited to delivery of low viscosity compositions, and in particular low molecular weight agents that have a moderate lipophilicity and no charge. Moreover, even upon successful crossing of the natural boundary, problems still exist with regard to maintaining the activity level of delivered agents and avoidance of foreign body and immune response.

What are needed in the art are devices and methods for delivery of bioactive agents. More specifically, what are needed are devices and methods that can successfully deliver a high viscosity composition that includes a bioactive agent and can also prevent targeting of the bioactive agent by the body's own defensive mechanisms.

SUMMARY

According to one embodiment, disclosed is a device for delivery of a composition across a dermal barrier. More specifically, the device may include a microneedle and a plurality of nanostructures fabricated on a surface thereof. The nanostructures can be arranged in a predetermined pattern. The device also includes the composition in fluid communication with the microneedle. More specifically, the composition includes a bioactive agent and can have a viscosity of greater than about 5 centipoise.

According to another embodiment, disclosed is a method for delivering a composition to a subject. The method includes penetrating the stratum corneum of the subject with a microneedle that is in fluid communication with the composition. The composition includes a bioactive agent and has a viscosity greater than about 5 centipoise. In addition, the microneedle includes a plurality of nanostructures formed on a surface thereof in a pattern. The method also includes transporting the bioactive agent through the microneedle at a rate of greater than about 0.4 $mg/hr/cm^2$ based upon the surface area of the microneedle.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

Figure 10A:
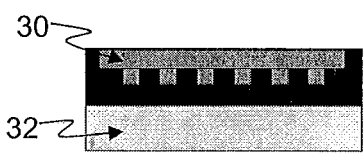
Figure 10B:
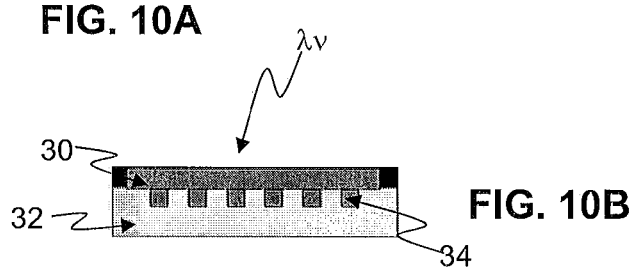
Figure 10C:
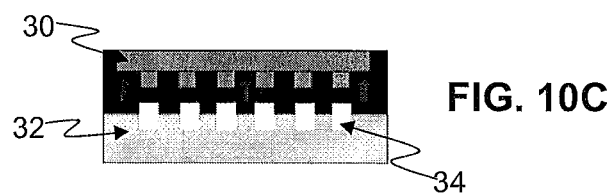

FIGS. 10A-10C schematically illustrate a nanoimprinting method as may be utilized in one embodiment in forming a device.

Figure 11A:
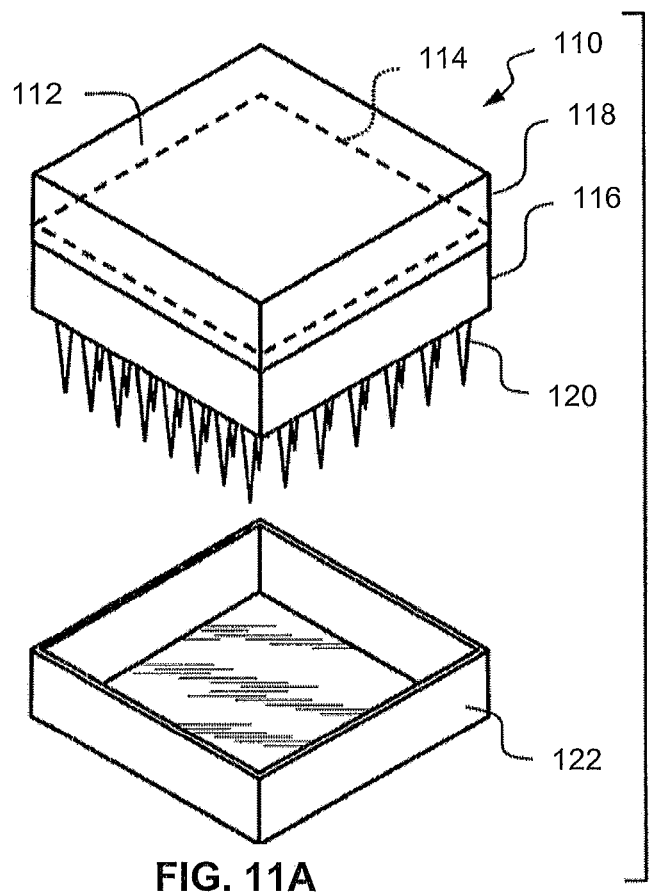
Figure 11B:
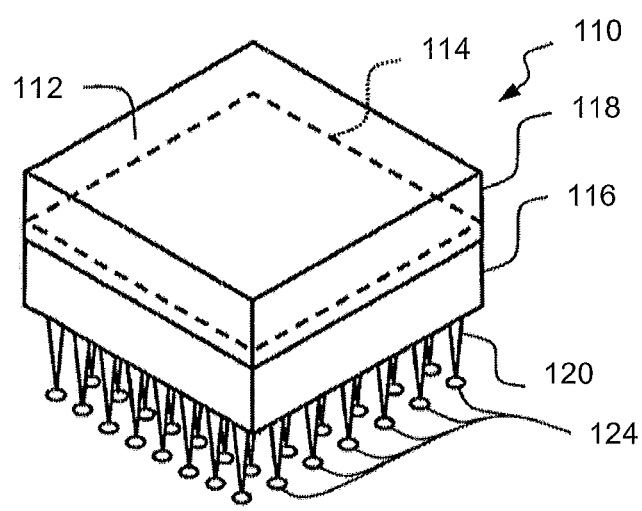

FIG. 11 schematically illustrates one embodiment of a device including a release liner (FIG. 11A) and following removal of the release liner (FIG. 11B).

Figure 12:
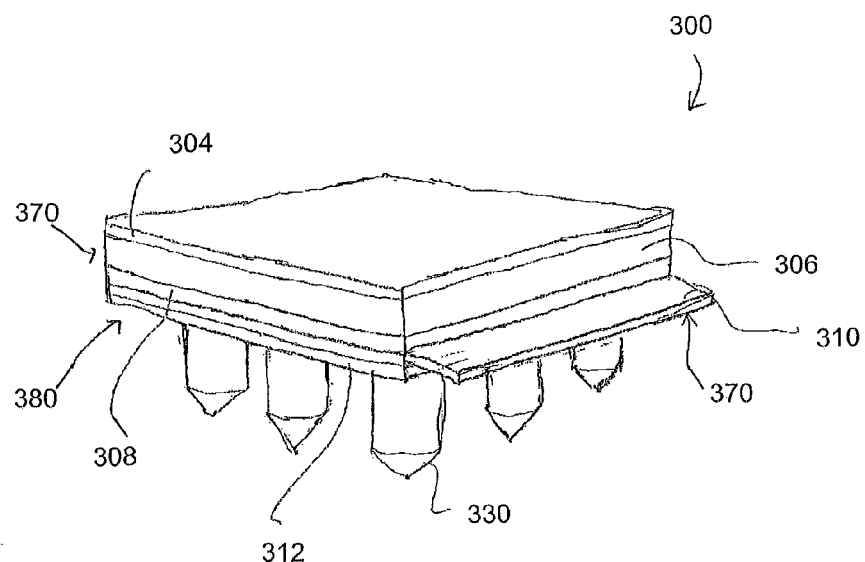

FIG. 12 is a perspective view of one embodiment of a transdermal patch prior to delivery of a drug compound.

Figure 13:
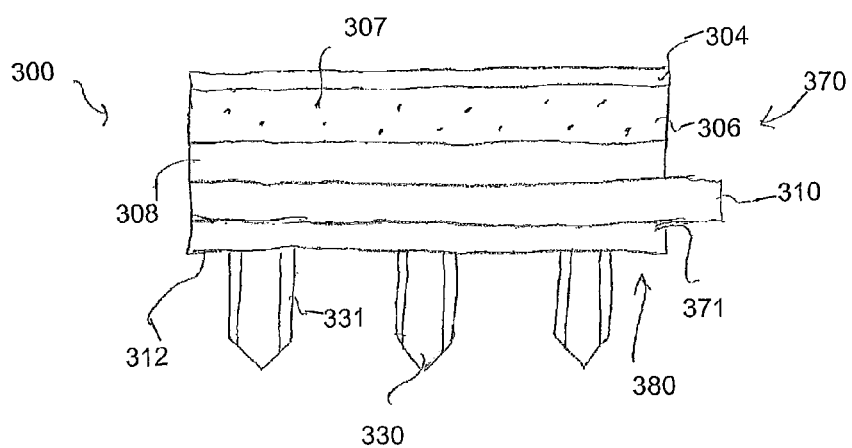

FIG. 13 is a front view of the patch of FIG. 12.

Figure 14:
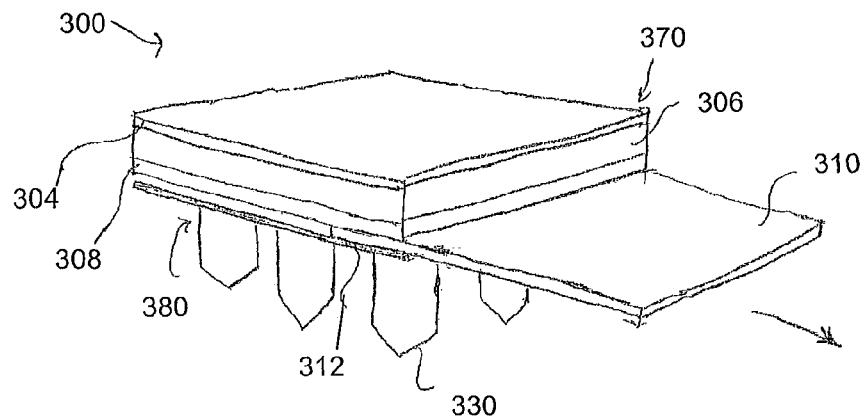

FIG. 14 is a perspective view of the patch of FIG. 12 in which the release member is partially withdrawn from the patch.

Figure 15:
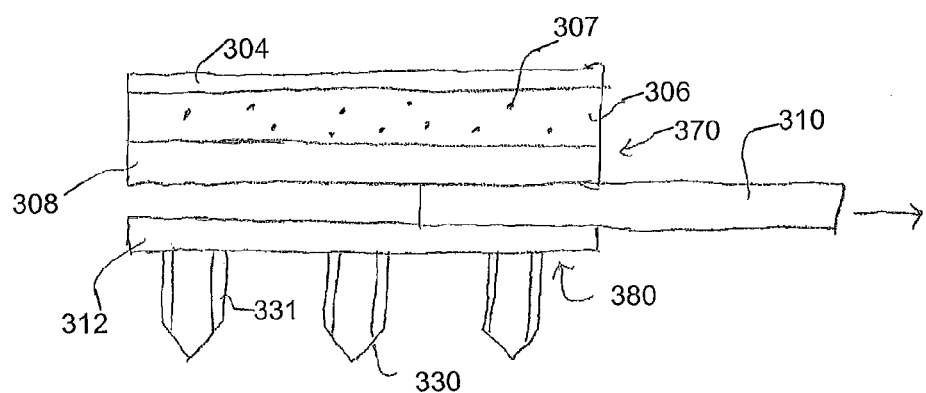

FIG. 15 is a front view of the patch of FIG. 14.

Figure 16:
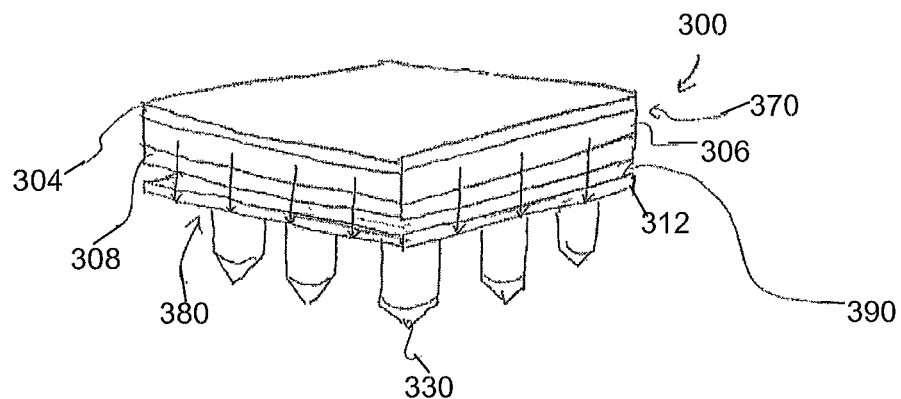

FIG. 16 is a perspective view of the transdermal patch of FIG. 12 after removal of the release member and during use.

Figure 17:
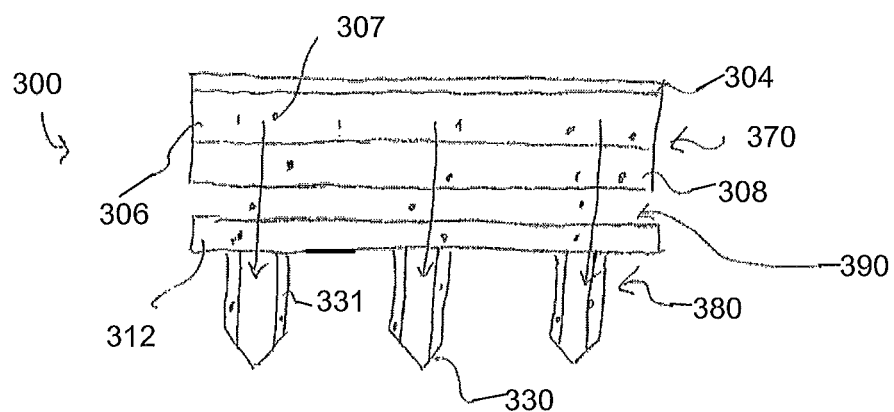

FIG. 17 is a front view of the patch of FIG. 16.

Figure 18:
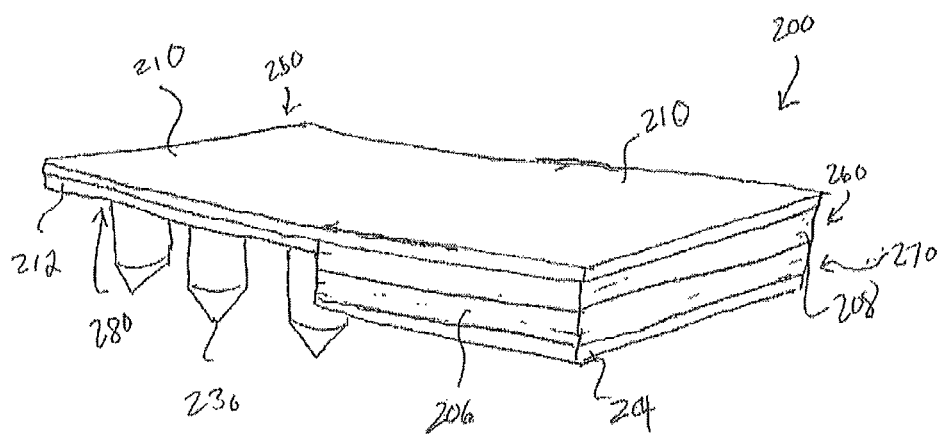

FIG. 18 is a perspective view of another embodiment of a transdermal patch prior to delivery of a drug compound.

Figure 19:
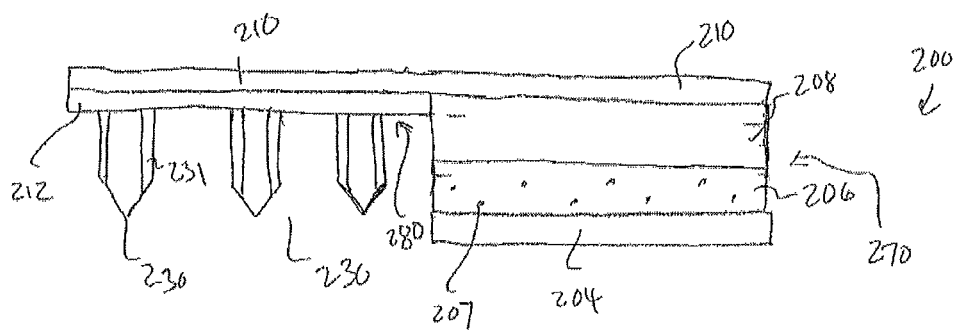

FIG. 19 is a front view of the patch of FIG. 18.

Figure 20:
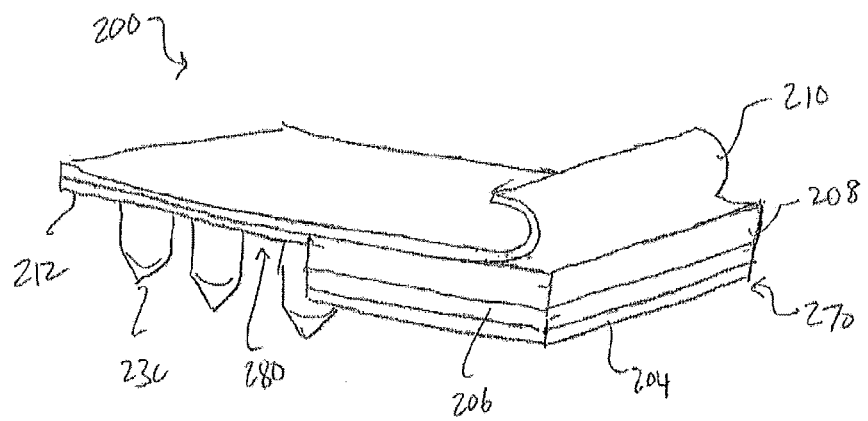

FIG. 20 is a perspective view of the patch of FIG. 18 in which the release member is partially peeled away from the patch.

Figure 21:
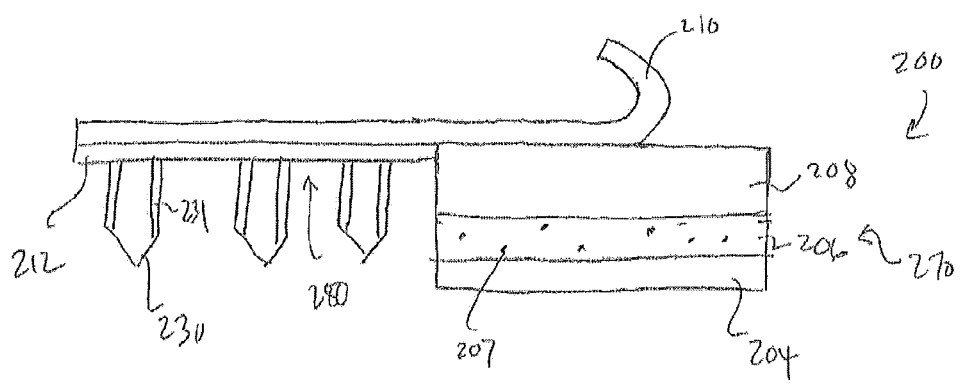

FIG. 21 is a front view of the patch of FIG. 20.

Figure 22:
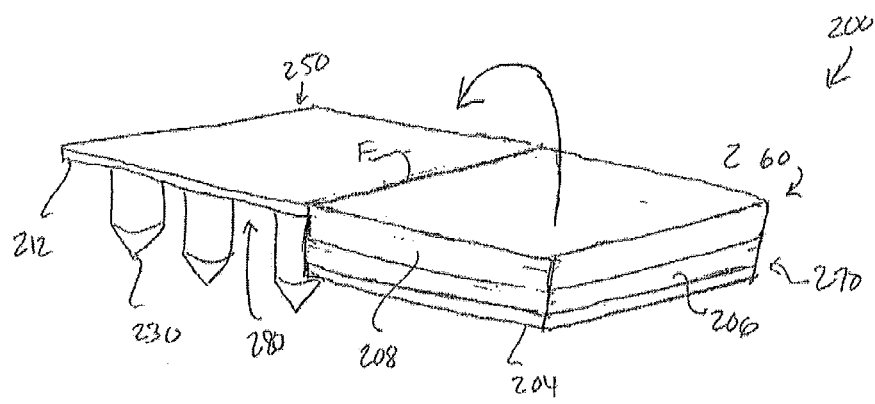

FIG. 22 is a perspective view of the patch of FIG. 18 in which the release member is completely peeled away from the patch.

Figure 23:
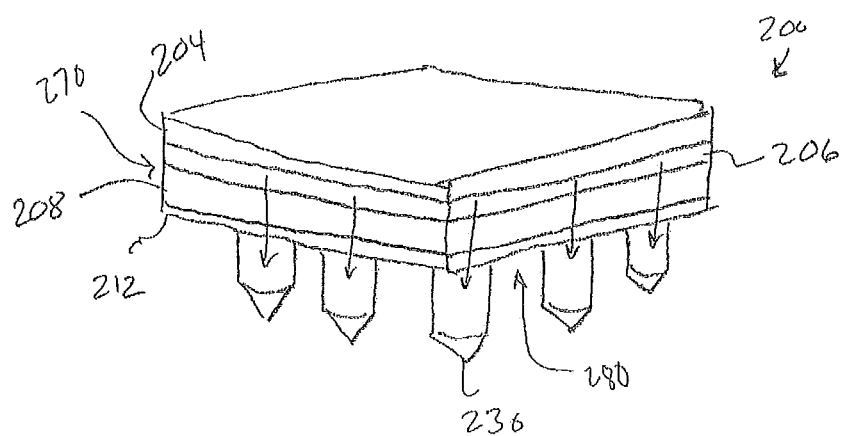

FIG. 23 is a perspective view of the transdermal patch of FIG. 18 after removal of the release member and during use.

FIGS. 24A-24E illustrate several nanotopography patterns as described herein.

FIG. 25 is an SEM of a film including a nanopatterned surface.

Figure 26A:
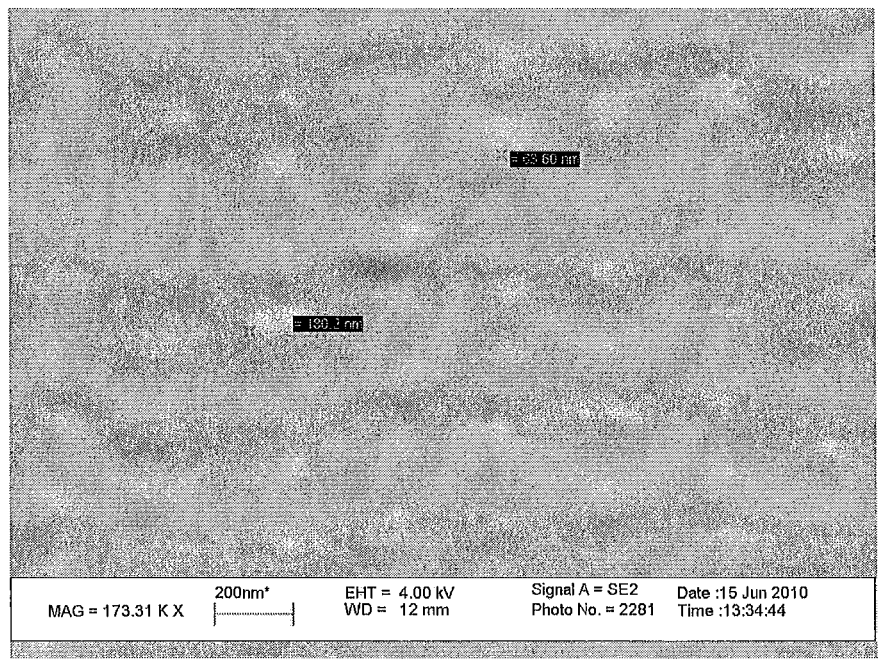
Figure 26B:
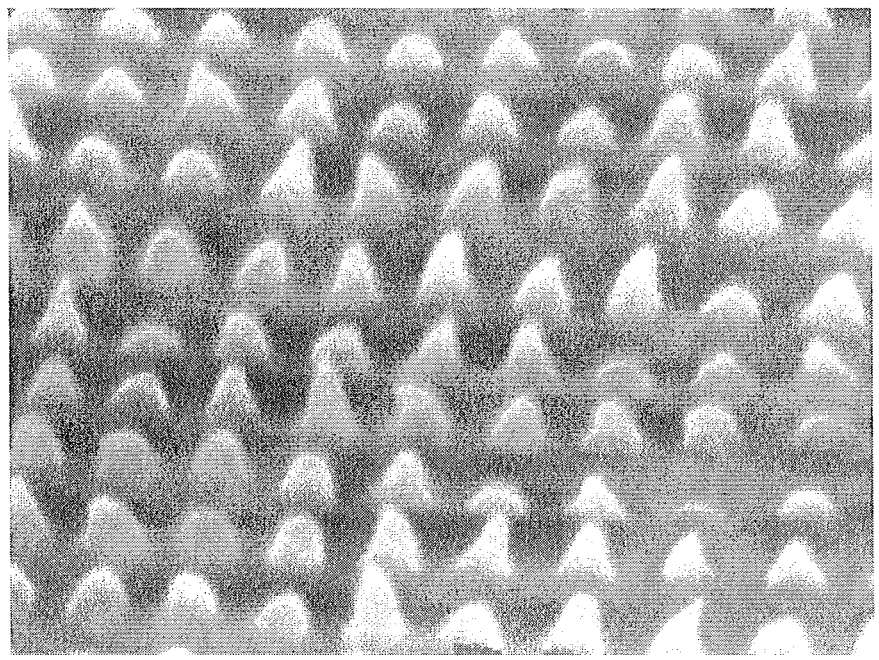

FIGS. 26A and 26B are two SEM of a film including another nanopatterned surface.

Figure 27:
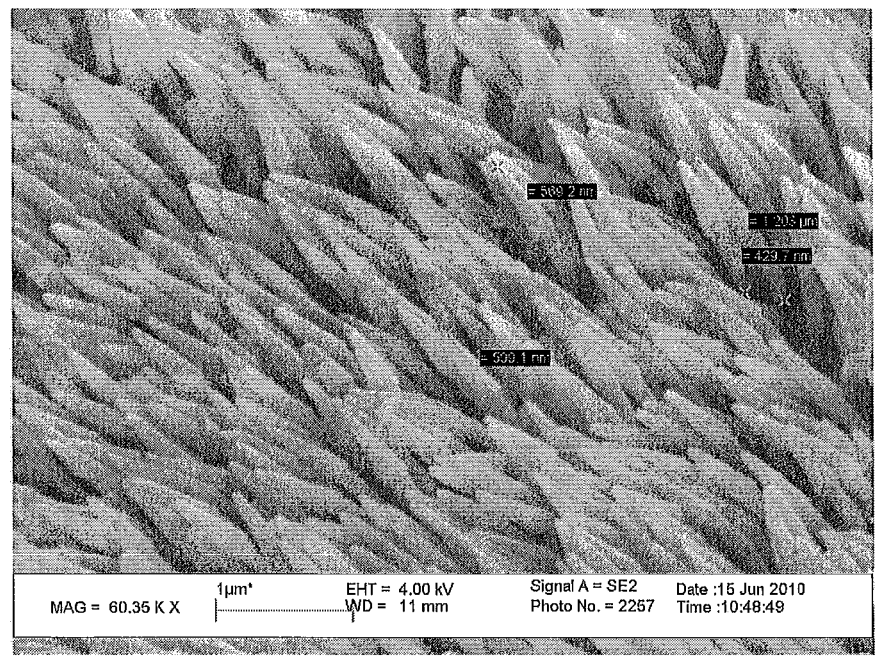

FIG. 27 is an SEM of a film including another nanopatterned surface.

Figure 28:
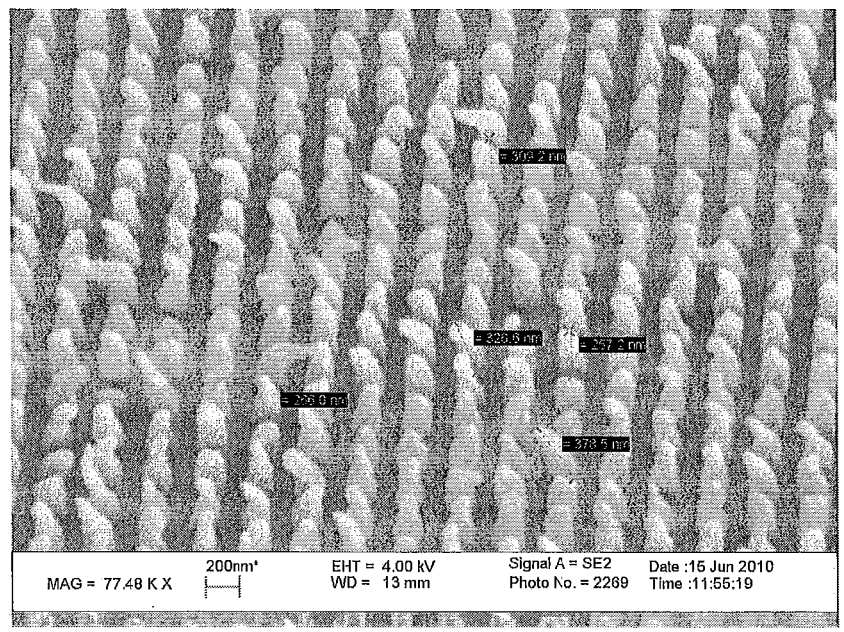

FIG. 28 is an SEM of a film including another nanopatterned surface.

Figure 29:
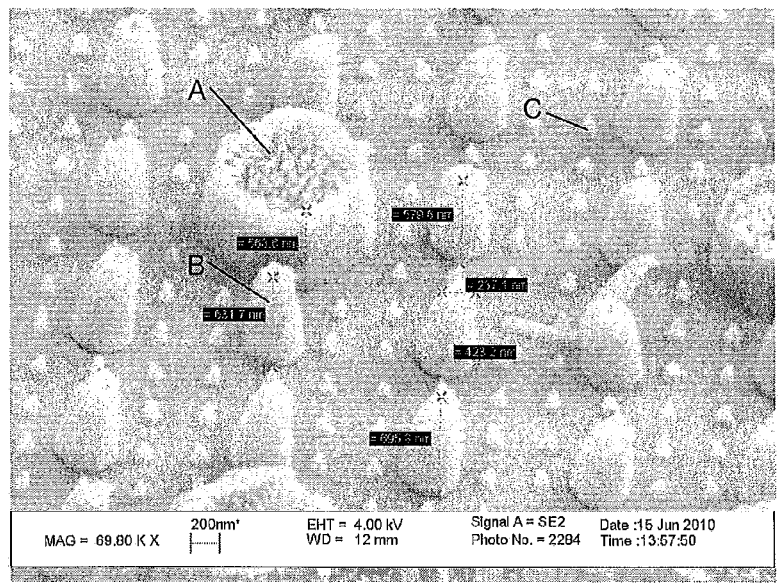

FIG. 29 is an SEM of a film including another nanopatterned surface.

Figure 30:
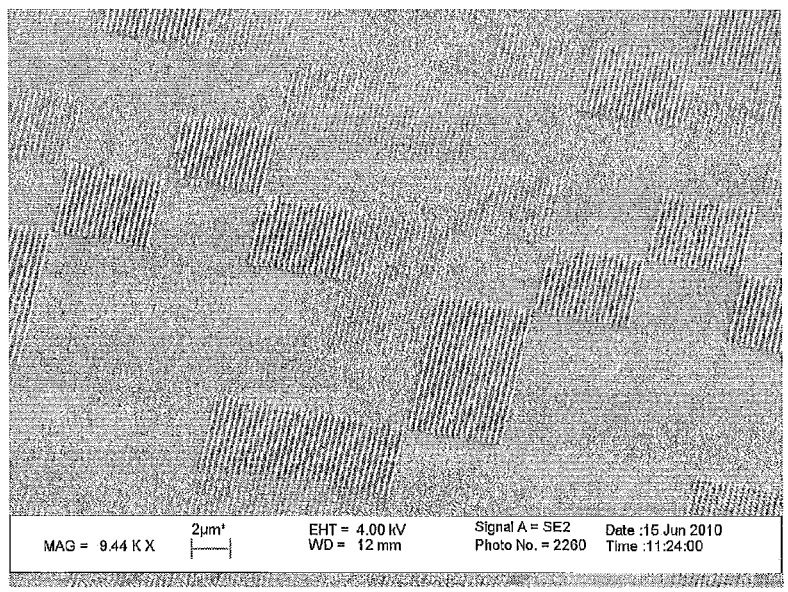

FIG. 30 is an SEM of a film including another nanopatterned surface.

Figure 31:
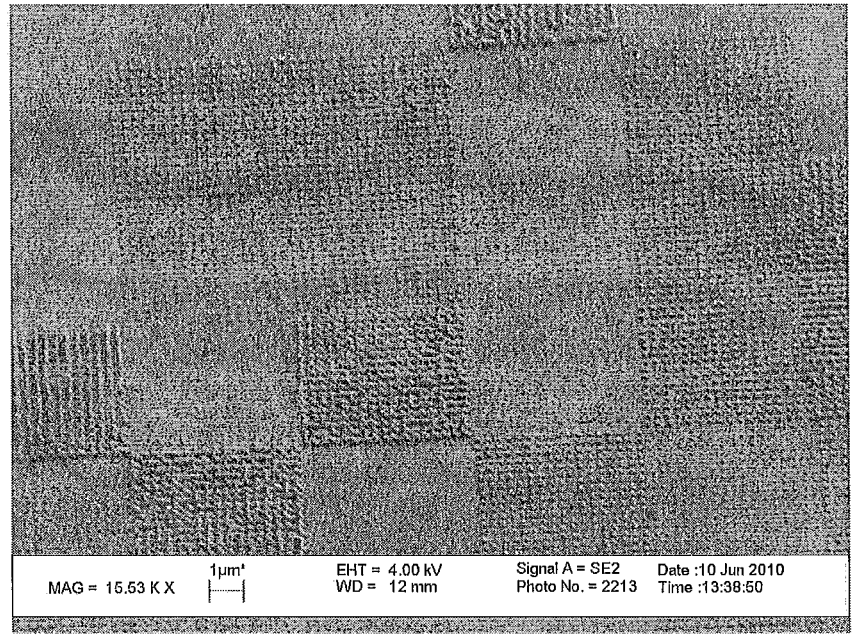

FIG. 31 is an SEM of a film including another nanopatterned surface.

Figure 32:
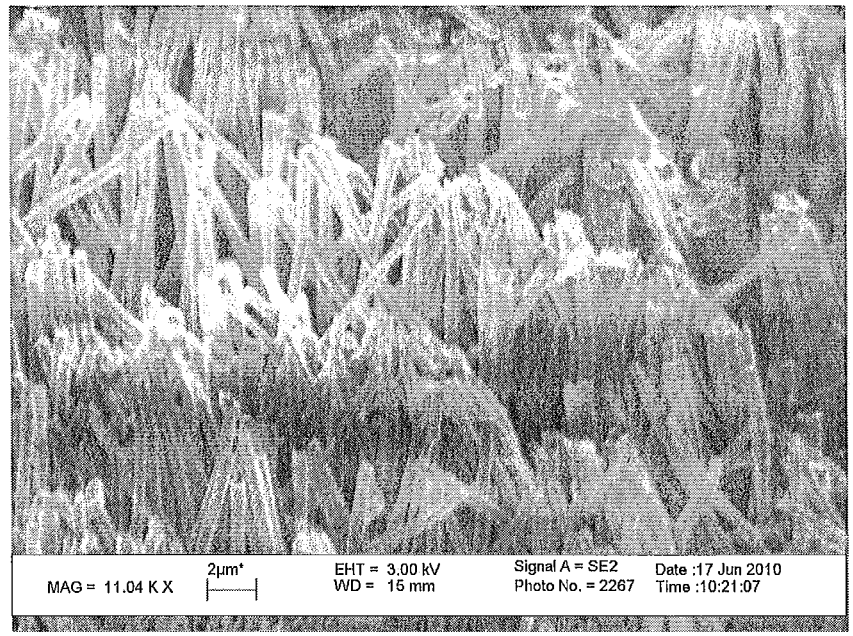

FIG. 32 is an SEM of a film including another nanopatterned surface.

Figure 33:
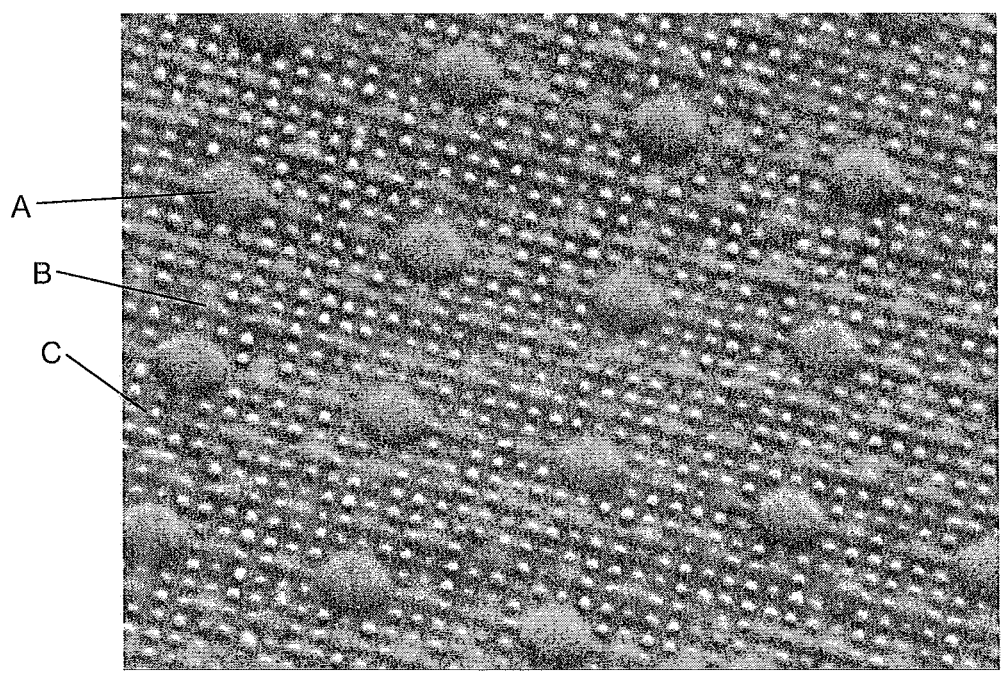
Figure 34:
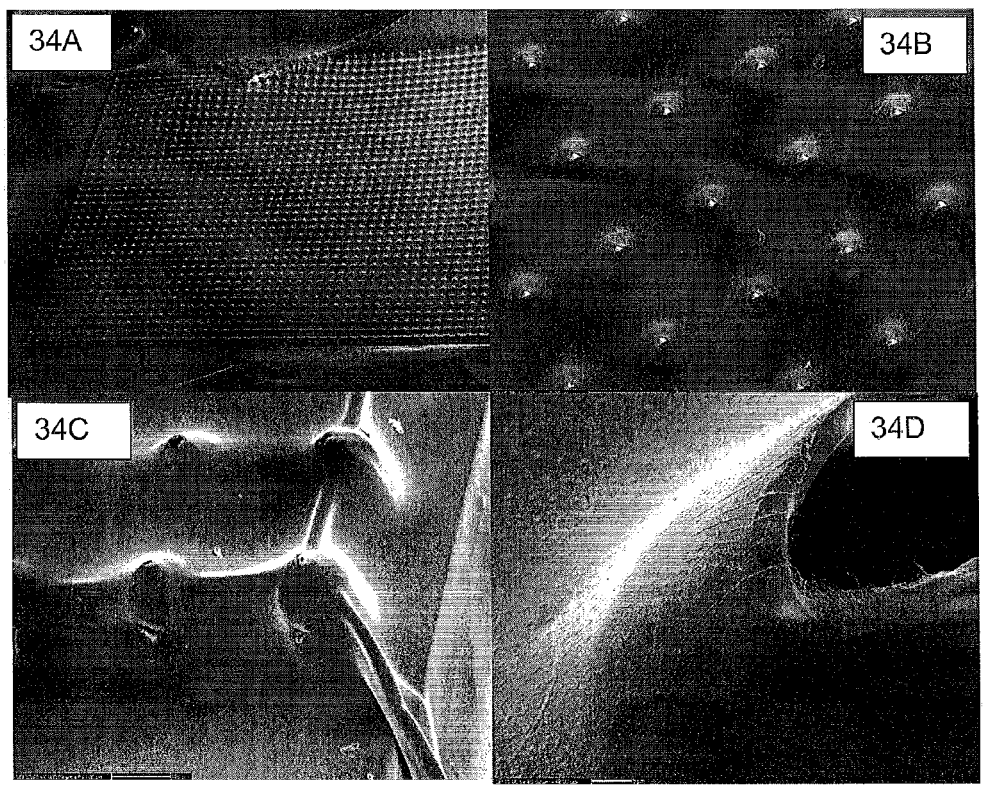

FIG. 33 is an SEM of a film including another nanopatterned surface.

FIGS. 34A-34D are images of a microneedle array as described herein at increasing magnification.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

Devices and methods are described herein that provide a route for delivering a composition including a bioactive agent across a dermal barrier of a subject, the transdermal delivery device including one or more microneedles. More specifically, the composition can have a high viscosity, and in particular a viscosity that in the past has not been considered deliverable by use of transdermal devices, e.g., a viscosity greater than about 5 centipoise. Methods can include delivery of the high viscosity bioactive agent to the subject at a useful rate, for instance at a rate of greater than about 5 mg/mL per hour. The high viscosity of the composition can be due to, for example, a high concentration of the bioactive agent in the composition, a high molecular weight bioactive agent in the composition, high molecular weight or high concentration adjuvants in the composition, or a combination of factors. For instance, the composition can include one or more high molecular weight bioactive agents, such as protein therapeutics having a molecular weight greater than about 100 kDa. In the past, it has proven difficult or impossible to obtain transdermal delivery of such bioactive agents due to an inability to breach the body's natural barriers.

Subjects as may benefit from the methods can include any animal subject in need of delivery of a bioactive agent. For instance a subject can be a human or any other mammal or animal as may benefit from the delivery methods.

The delivery method utilizes a transdermal delivery device that includes one or more microneedles and a pattern of structures fabricated on a surface of at least one of the microneedles. In addition, at least a portion of the structures fabricated on a surface of the microneedle are fabricated on a nanometer scale. As utilized herein, the term 'fabricated' generally refers to a structure that has been specifically designed, engineered, and/or constructed so as to exist at a surface of a microneedle and is not to be equated with a surface feature that is merely an incidental product of the formation process. Thus, the transdermal delivery device will include a predetermined pattern of nanostructures, i.e., a nanotopography, on the surface of a microneedle.

Without wishing to be bound by any particular theory, it is believed that through interaction between the nanotopography on a surface of the microneedle and surrounding biological materials or structures, the microneedle may regulate and/or modulate membrane potential, membrane proteins, and/or intercellular junctions (e.g., tight junctions, gap junctions, and/or desmasomes) of and between cells in the area surrounding the microneedle. More specifically, it is believed that interaction between the nanotopography of the microneedle and the surrounding biological materials can rearrange epithelial tight junctions of the dermal tissue and temporarily increase porosity of the local barrier structures. This can encourage transport of the high viscosity composition carrying the bioactive agent across not only the dermal barrier.

In addition, it is believed that interaction between the nanotopography of the device and the surrounding biological structures can encourage transport of the composition carrying the bioactive agent across other natural barriers to systemic delivery, beyond the dermal barriers. Specifically, through utilization of the nanostructured transdermal delivery devices, the permeability is increased not only in tissue in the immediate, contacting area of the device, but also in surrounding tissue. It is believed that increased permeability can occur not only between cells in contact with the microneedle, but this effect can be perturbed to other cells in the area, including cells of different tissue types. This can translate the increased porosity effect to nearby structures and tissue types, which can increase porosity of nearby vasculature.

The interaction between the device and the contacting tissue is understood to lead to the rearrangement of epithelial tight junctions of the dermal tissue, and this instigates a cascade response that transfers a similar effect to the cells of the local blood vessels, for instance cells of both the basement membrane and the endothelium of a local capillary. This can lead to fenestration of the capillary wall, allowing entry of a bioactive agent directly to the cardiovascular system. This can significantly increase uptake of the bioactive agent by the subject's system.

By use of the devices, delivery of a high viscosity composition including one or more bioactive agents can be improved. A high viscosity composition can have a viscosity of, for example, greater than about 5 centipoise, greater than about 10 centipoise, or greater than about 25 centipoise. In one embodiment, the composition can have a viscosity of from about 10 centipoise to about 50 centipoise, for instance, from about 30 centipoise to about 40 centipoise.

Viscosity of a composition can be determined according to standard practice. For instance, one approach to measuring viscosity calls for inserting a piston into a closed vessel containing the sample fluid, and then measuring the torque required to rotate the piston in the vessel. While this approach is adequate for measuring the viscosity of larger fluid samples, it offers the disadvantage of requiring and consuming relatively large volumes of sample fluid. Such volumes may not be available for analysis, particularly in the context of biological analysis.

In accordance with an alternative method, diffusion of a marker of known size and diffusion coefficient (i.e. a fluorescently labeled bead or macromolecule) across a microfluidic free interface created within the composition may be utilized to determine the viscosity. Such a technique is applicable to analysis of the viscosity of biological or physiological samples, as the dimensions of the microfluidic channels in which diffusion occurs occupies relatively small volumes.

Viscosity of a composition can be determined through use of standard meters, for instance a capillary viscometer as is known in the art. Exemplary rheometers as may be utilized include, without limitation, the Brookfield™ programmable rheometer, LV-DV-III, an Ostwald viscosity meter, a VROC® viscometer rheometer-on-a-chip, which is a micron scale viscosity sensor chip for small samples, a Haake Viscotester™ VT 550 rheometer, and the like.

The devices can deliver a high viscosity composition at a useful rate to a subject in need thereof. For instance, a high viscosity composition can be transdermally delivered at a rate of greater than about 0.4 mg/hr/cm$^2$, greater than about 1 mg/hr/cm$^2$, greater than about 3 mg/hr/cm$^2$, or greater than about 6 mg/hr/cm$^2$, based upon the surface area of the microneedle.

There is no particular limitation to bioactive agents as may be delivered by use of the methods. Bioactive agents can encompass natural or synthetic agents, small molecule agents, and so forth. In one embodiment, methods may be utilized for delivery of high molecular weight bioactive agents (e.g., non-proteinaceous synthetic or natural bioactive agents defining a molecular weight greater than about 400 Da, greater than about 10 kDa, greater than about 20 kDa, or greater than about 100 kDa, e.g., about 150 kDa).

In one particular example, a bioactive agent delivered according to the methods can be a high molecular weight protein therapeutic. As utilized herein, the term 'protein therapeutics' generally refers to any biologically active proteinaceous compound including, without limitation, natural, synthetic, and recombinant compounds, fusion proteins, chimeras, and so forth, as well as compounds including the 20 standard amino acids and/or synthetic amino acids. By way of example, a protein therapeutic having a molecular weight of greater than about 100 kDa, or greater than about 125 kDa, for instance from about 125 kDa to about 200 kDa, or from about 150 kDa to about 200 kDa, can be delivered transdermally via the methods.

In one embodiment, the methods and devices may be utilized for delivery of a composition including a high concentration of a bioactive agent, either a large molecular weight bioactive agent or a small molecule bioactive agent. By way of example, a composition can include a bioactive agent in a concentration of greater than about 5 mg/mL, greater than about 10 mg/mL, greater than about 30 mg/mL, greater than about 50 mg/mL, greater than about 100 mg/mL, or greater than about 200 mg/mL. For instance, the composition can include a bioactive agent in a concentration of from about 35 mg/mL to about 500 mg/mL or from about 50 mg/mL to about 400 mg/mL.

Agents may include proteinaceous agents such as insulin, immunoglobulins (e.g., IgG, IgM, IgA, IgE), TNF-α, antiviral medications, and so forth; polynucleotide agents including plasmids, siRNA, RNAi, nucleoside anticancer drugs, vaccines, and so forth; and small molecule agents such as alkaloids, glycosides, phenols, and so forth. Agents may include anti-infection agents, hormones, drugs that regulate cardiac action or blood flow, pain control, and so forth. Still other substances which may be delivered in accordance with the present disclosure are agents useful in the prevention, diagnosis, alleviation, treatment, or cure of disease. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents as described in U.S. Pat. No. 6,569,143 entitled "Method of Intradermally injecting Substances", the entire content of which is incorporated herein by reference. Vaccine formulations may include an antigen or antigenic composition capable of eliciting an immune response against a human pathogen or from other viral pathogens.

In one embodiment, methods may be utilized in treatment of a chronic condition, such as rheumatoid arthritis, to deliver a steady flow of an agent, to a subject in need thereof. RA drugs that can be delivered can include symptom suppression compounds, such as analgesics and anti-inflammatory drugs including both steroidal and non-steroidal anti-inflammatory drugs (NSAID), as well as disease-modifying antirheumatic drugs (DMARDs).

RA drugs can include, without limitation, one or more analgesics, anti-inflammatories, DMARDs, herbal-based drugs, and combinations thereof. Specific compounds can, of course, fall under one or more of the general categories described herein. For instance, many compounds function as both an analgesic and an anti-inflammatory; herbal-based drugs can likewise function as a DMARD as well as an anti-inflammatory. Moreover, multiple compounds that can fall under a single category can be delivered. For instance, methods can be utilized to deliver multiple analgesics, such as acetaminophen with codeine, acetaminophen with hydrocodone (vicodin), and so forth.

A composition may include one or more bioactive agents in conjunction with other components as are generally known in the art. For instance, a composition can include one or more pharmaceutically acceptable excipients. As utilized herein, the term "excipient" generally refers to any substance, not itself a bioactive agent, used in conjunction with the bioactive agent(s) delivered to a subject to improve one or more characteristics, such as its handling or storage properties or to permit or facilitate formation of a dose unit of the composition. Excipients include, by way of illustration and not limitation, solvents (e.g., lower alcohol, such as ethanol or isopropanol; or water), penetration enhancers, thickening agents, wetting agents, lubricants, emollients, substances added to mask or counteract a disagreeable odor or flavor, fragrances, adjuvants, and substances added to improve appearance or texture of the composition or delivery device. Any such excipients can be used in any amounts as are generally known.

Non-limiting examples of penetration enhancing agents include $C_8$-$C_{22}$ fatty acids such as isostearic acid, octanoic acid, and oleic acid; $C_8$-$C_{22}$ fatty alcohols such as oleyl alcohol and lauryl alcohol; lower alkyl esters of $C_8$-$C_{22}$ fatty acids such as ethyl oleate, isopropyl myristate, butyl stearate, and methyl laurate; di(lower)alkyl esters of $C_6$-$C_{22}$ diacids such as diisopropyl adipate; monoglycerides of $C_8$-$C_{22}$ fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes. Additional penetration enhancers suitable for use can also be found in U.S. Published Patent Application No. 2002/0111377, which is incorporated herein by reference. One or more penetration enhancers, when present, can generally be present in a total amount of from about 0.01% to about 25%, or from about 0.1% to about 15% by weight of the composition.

Thickening agents (also referred to herein as gelling agents) may include anionic polymers such as polyacrylic acid (Carbopol® by Noveon, Inc., Cleveland, Ohio), carboxypolymethylene, carboxymethylcellulose and the like, including derivatives of Carbopol® polymers, such as Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3, and other polymers such as Pemulen® polymeric emulsifiers, and Noveon® polycarbophils. Thickening agents, when present, can generally be present in a total amount by weight of from about 0.1% to about 15%, from about 0.25% to about 10%, or from about 0.5% to about 5%.

Additional thickening agents, enhancers and adjuvants may generally be found in Remington's The Science and Practice of Pharmacy as well as the Handbook of Pharmaceutical Excipients, Arthur H. Kibbe ed. 2000.

One or more neutralizing agents can be present to assist in forming a gel. Suitable neutralizing agents include sodium hydroxide (e.g., as an aqueous mixture), potassium hydroxide (e.g., as an aqueous mixture), ammonium hydroxide (e.g., as an aqueous mixture), triethanolamine, tromethamine (2-amino 2-hydroxymethyl-1,3 propanediol), aminomethyl propanol (AMP), tetrahydroxypropyl ethylene diamine, diisopropanolamine, Ethomeen C-25 (Armac Industrial Division), Di-2 (ethylhexyl) amine (BASF-Wyandotte Corp., Intermediate Chemicals Division), triamylamine, Jeffamine D-1000 (Jefferson Chemical Co.), b-Dimethylaminopropionitrite (American Cyanamid Co.), Armeen CD (Armac Industrial Division), Alamine 7D (Henkel Corporation), dodecylamine and morpholine. The neutralizing agent can be present in an amount sufficient to form a gel which is suitable for contact with the skin of a mammal, e.g., up to about 10% by weight of the composition, for example between about 0.1% and about 5% by weight of the composition.

A composition may include one or more pharmaceutically acceptable wetting agents (also referred to as surfactants) as excipients. Non-limiting examples of surfactants can include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. One or more wetting agents, when present, generally constitute in total from about 0.25% to about 15%, from about 0.4% to about 10%, or from about 0.5% to about 5%, of the total weight of the composition.

A composition may include one or more pharmaceutically acceptable lubricants (including anti-adherents and/or glidants) as excipients. Suitable lubricants include, without limiation, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, when, can generally constitute from about 0.1% to about 10%, from about 0.2% to about 8%, or from about 0.25% to about 5%, of the total weight of the composition.

A composition may include one or more emollients. Illustrative emollients include, without limitation, mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate, isopropyl palmitate, lecithin, allyl caproate, althea officinalis extract, arachidyl alcohol, argobase EUC, Butylene glycol dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75 lanolin, sorbitan laurate, walnut oil, wheat germ oil super refined almond, super refined sesame, super refined soybean, octyl palmitate, caprylic/capric triglyceride and glyceryl cocoate. A composition may include one or more emollients in a total amount of from about 1% to about 30%, from about 3% to about 25%, or from about 5% to about 15%, by weight of the composition.

A composition may include one or more antimicrobial preservative. Illustrative anti-microbial preservatives include, without limitation, benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate, or thimerosal. One or more anti-microbial preservatives, when present, can generally be present in a total amount of from about 0.1% to about 5%, from about 0.2% to about 3%, or from about 0.3% to about 2%, by weight of the composition.

A composition may include one or more emulsifying agents. As utilized herein, the term "emulsifying agent" generally refers to an agent capable of lowering surface tension between a non-polar and polar phase and includes compounds defined as "self-emulsifying" agents. Suitable emulsifying agents can come from any class of pharmaceutically acceptable emulsifying agents including carbohydrates, proteins, high molecular weight alcohols, wetting agents, waxes and finely divided solids. One or more emulsifying agents, when present, can be present in a composition in a total amount of from about 1% to about 15%, from about 1% to about 12%, from about 1% to about 10%, or from about 1% to about 5% by weight of the composition.

The composition can be prepared by any technique known to a person of ordinary skill in the art of pharmacy, pharmaceutics, drug delivery, pharmacokinetics, medicine or other related discipline that comprises admixing one or more excipients with a therapeutic agent to form a composition, drug delivery system or component thereof.

A transdermal delivery device may be constructed from a variety of materials, including metals, ceramics, semiconductors, organics, polymers, etc., as well as composites thereof. By way of example, pharmaceutical grade stainless steel, titanium, nickel, iron, gold, tin, chromium, copper, alloys of these or other metals, silicon, silicon dioxide, and polymers may be utilized. Typically, the device is formed of a biocompatible material that is capable of carrying a pattern of structures as described herein on a surface. The term "biocompatible" generally refers to a material that does not substantially adversely affect the cells or tissues in the area where the device is to be delivered. It is also intended that the material does not cause any substantially medically undesirable effect in any other areas of the living subject. Biocompatible materials may be synthetic or natural. Some examples of suitable biocompatible materials, which are also biodegradable, include polymers of hydroxy acids such as lactic acid and glycolic acid polylactide, polyglycolide, polylactide-co-glycolide, copolymers with polyethylene glycol, polyanhydrides, poly(ortho)esters, polyurethanes, poly(butyric acid), poly(valeric acid), and poly(lactide-co-caprolactone). Other suitable materials may include, without limitation, polycarbonate, polymethacrylic acid, ethylenevinyl acetate, polytetrafluorethylene, and polyesters. The device may likewise be non-porous or porous in nature, may be homogeneous or heterogeneous across the device with regard to materials, geometry, solidity, and so forth, and may have a rigid fixed or a semi-fixed shape.

Figure 1:
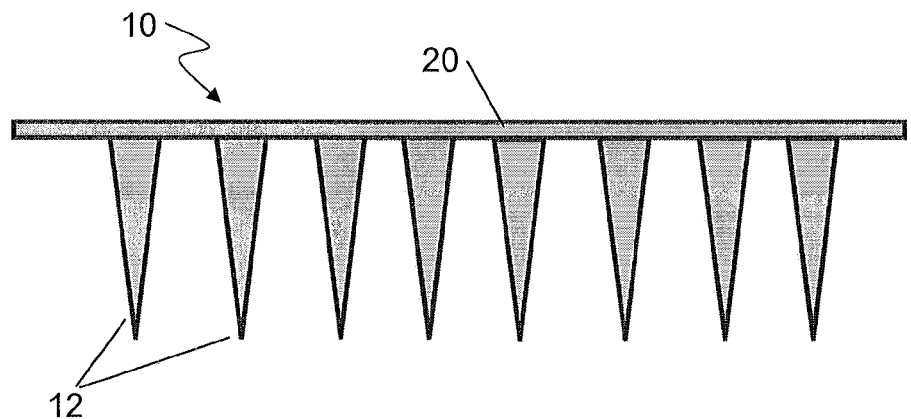
FIG. 1 illustrates one embodiment of a microneedle device.
Figure 2:
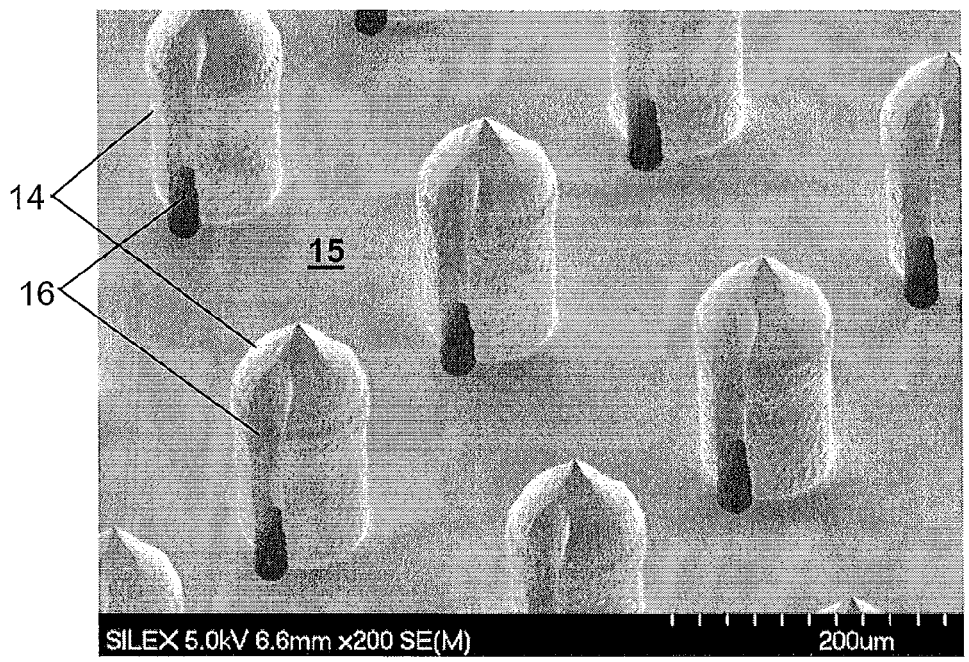
FIG. 2 illustrates another embodiment of a microneedle device.

FIG. 1 illustrates a typical microneedle transdermal delivery device 10. As may be seen, the device includes an array of individual needles 12; each formed to a size and shape so as to penetrate a biological barrier without breakage of the individual microneedles. Microneedles may be solid, as in FIG. 1, porous, or may include a hollow portion. A microneedle may include a hollow portion, e.g., an annular bore that may extend throughout all or a portion of the needle, extending parallel to the direction of the needle or branching or exiting at a side of the needle, as appropriate. For example, FIG. 2 illustrates an array of microneedles 14 each including a channel 16 in a side of the needles as may be utilized for, e.g., delivery of an agent to a subdermal location. For instance, a channel 16 may be in at least partial alignment with an aperture in base 15 so as to form a junction between the aperture and channel 16 allowing the passage of a substance through the channel 16.

The dimensions of the channel 16, when present, can be specifically selected to induce capillary flow of a composition including a bioactive agent. Capillary flow generally occurs when the adhesive forces of a fluid to the walls of a channel are greater than the cohesive forces between the liquid molecules. Specifically, capillary pressure is inversely proportional to the cross-sectional dimension of the channel 16 and directly proportional to the surface tension of the liquid, multiplied by the cosine of the contact angle of the fluid in contact with the material forming the channel. Thus, to facilitate capillary flow in the patch, the cross-sectional dimension (e.g., width, diameter, etc.) of the channel 16 may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel 16. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or length vary as a function of length, the aspect ratio can be determined from the average dimensions.

It should be understood that the number of microneedles shown in the figures is for illustrative purposes only. The actual number of microneedles used in a microneedle assembly may, for example, range from about 500 to about 10,000, in some embodiments from about 2,000 to about 8,000, and in some embodiments, from about 4,000 to about 6,000.

An individual microneedle may have a straight or a tapered shaft. In one embodiment, the diameter of a microneedle may be greatest at the base end of the microneedle and taper to a point at the end distal the base. A microneedle may also be fabricated to have a shaft that includes both a straight (untapered) portion and a tapered portion.

A microneedle may be formed with a shaft that is circular or non-circular in cross-section. For example, the cross-section of a microneedle may be polygonal (e.g. star-shaped, square, triangular), oblong, or any other shape. The shaft may have one or more bores and/or channels.

The size of individual needles may be optimized depending upon the desired targeting depth, the strength requirements of the needle to avoid breakage in a particular tissue type, etc. For instance, the cross-sectional dimension of a transdermal microneedle may be between about 10 nanometers (nm) and 1 millimeter (mm), or between about 1 micrometer (μm) and about 200 micrometers, or between about 10 micrometers and about 100 micrometers. The outer diameter may be between about 10 micrometers and about 100 micrometers and the inner diameter of a hollow needle may be between about 3 micrometers and about 80 micrometers. The tip typically has a radius that is less than or equal to about 1 micrometer.

The length of a microneedle will generally depend upon the desired application. For instance, a microneedle may be from about 1 micrometer to about 1 millimeter in length, for instance about 500 micrometers or less, or from about 10 micrometers to about 500 micrometers, or from about 30 micrometers to abut 200 micrometers.

An array of microneedles need not include microneedles that are all identical to one another. An array may include a mixture of microneedles having various lengths, outer diameters, inner diameters, cross-sectional shapes, nanostructured surfaces, and/or spacings between the microneedles. For example, the microneedles may be spaced apart in a uniform manner, such as in a rectangular or square grid or in concentric circles. The spacing may depend on numerous factors, including height and width of the microneedles, as well as the amount and type of any substance that is intended to be moved through the microneedles. While a variety of arrangements of microneedles is useful, a particularly useful arrangement of microneedles is a "tip-to-tip" spacing between microneedles of about 50 micrometers or more, in some embodiments about 100 to about 800 micrometers, and in some embodiments, from about 200 to about 600 micrometers.

Referring again to FIG. 1, microneedles may be held on a substrate 20 (i.e., attached to or unitary with a substrate) such that they are oriented perpendicular or at an angle to the substrate. In one embodiment, the microneedles may be oriented perpendicular to the substrate and a larger density of microneedles per unit area of substrate may be provided. However, an array of microneedles may include a mixture of microneedle orientations, heights, materials, or other parameters. The substrate 20 may be constructed from a rigid or flexible sheet of metal, ceramic, plastic or other material. The substrate 20 can vary in thickness to meet the needs of the device, such as about 1000 micrometers or less, in some embodiments from about 1 to about 500 micrometers, and in some embodiments, from about 10 to about 200 micrometers.

Figure 3:
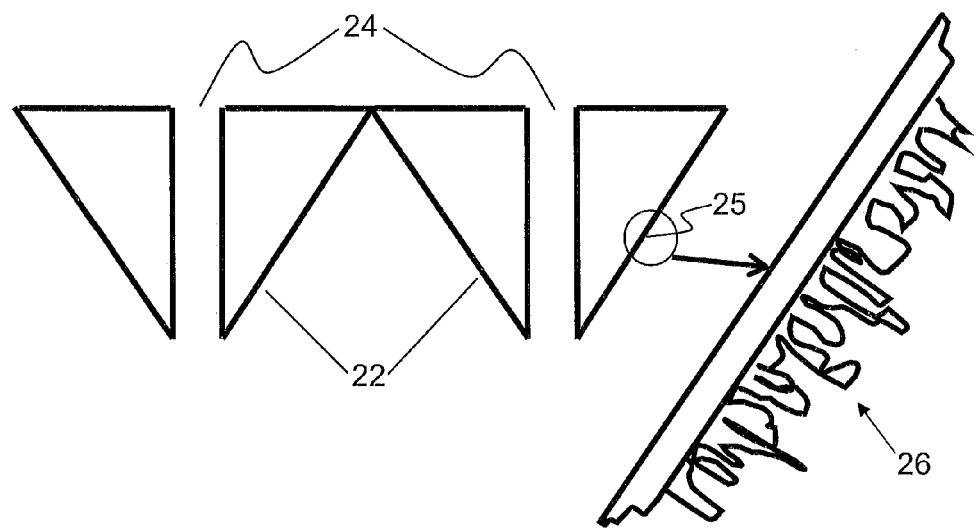
FIG. 3 illustrates one embodiment of a microneedle including a surface that defines a nanotopography that may interact with an extracellular matrix (ECM).

A microneedle surface may define a nanotopography thereon in a random or organized pattern. FIG. 3 schematically illustrates the ends of two representative microneedles 22. Microneedles 22 define a central bore 24 as may be used for delivery of an agent via the microneedles 22. The surface 25 of microneedles 22 define nanotopography 26. In this particular embodiment, the nanotopography 26 defines a random pattern on the surface 25 of the microneedle 22.

A microneedle may include a plurality of identical structures formed on a surface or may include different structures formed of various sizes, shapes and combinations thereof. A predetermined pattern of structures may include a mixture of structures having various lengths, diameters, cross-sectional shapes, and/or spacings between the structures. For example, the structures may be spaced apart in a uniform manner, such as in a rectangular or square grid or in concentric circles. In one embodiment, structures may vary with regard to size and/or shape and may form a complex nanotopography. For example, a complex nanotopography may define a fractal or fractal-like geometry.

As utilized herein, the term "fractal" generally refers to a geometric or physical structure having a fragmented shape at all scales of measurement between a greatest and a smallest scale such that certain mathematical or physical properties of the structure behave as if the dimensions of the structure are greater than the spatial dimensions. Mathematical or physical properties of interest may include, for example, the perimeter of a curve or the flow rate in a porous medium. The geometric shape of a fractal may be split into parts, each of which defines self-similarity. Additionally, a fractal has a recursive definition and has a fine structure at arbitrarily small scales.

As utilized herein, the term "fractal-like" generally refers to a geometric or physical structure having one or more, but not all, of the characteristics of a fractal. For instance, a fractal-like structure may include a geometric shape that includes self-similar parts, but may not include a fine structure at an arbitrarily small scale. In another example, a fractal-like geometric shape or physical structure may not decrease (or increase) in scale equally between iterations of scale, as may a fractal, though it will increase or decrease between recursive iterations of a geometric shape of the pattern. A fractal-like pattern may be simpler than a fractal. For instance, it may be regular and relatively easily described in traditional Euclidean geometric language, whereas a fractal may not.

A microneedle surface defining a complex nanotopography may include structures of the same general shape (e.g., pillars) and the pillars may be formed to different scales of measurement (e.g., nano-scale pillars as well as micro-scale pillars). In another embodiment, a microneedle may include at a surface structures that vary in both scale size and shape or that vary only in shape while formed to the same nano-sized scale. Additionally, structures may be formed in an organized array or in a random distribution. In general, at least a portion of the structures may be nanostructures formed on a nano-sized scale, e.g., defining a cross-sectional dimension of less than about 500 nanometers, for instance less than about 400 nanometers, less than about 250 nanometers, or less than about 100 nanometers. The cross sectional dimension of the nanostructures can generally be greater than about 5 nanometers, for instance greater than about 10 nanometers, or greater than about 20 nanometers. For example, the nanostructures can define a cross sectional dimension between about 5 nanometers and about 500 nanometers, between about 20 nanometers and about 400 nanometers, or between about 100 nanometers and about 300 nanometers. In cases where the cross sectional dimension of a nanostructure varies as a function of height of the nanostructure, the cross sectional dimension can be determined as an average from the base to the tip of the nanostructures, or as the maximum cross sectional dimension of the structure, for example the cross sectional dimension at the base of a cone-shaped nanostructure.

Figure 4:
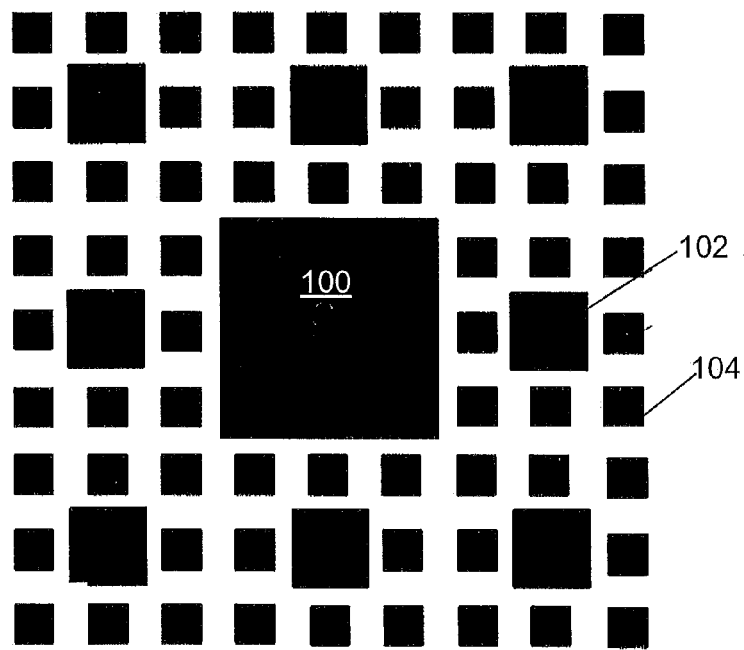
FIG. 4 illustrates one embodiment of a complex pattern that may be formed on a microneedle surface.

FIG. 4 illustrates one embodiment of a complex nanotopography as may be formed on a surface. This particular pattern includes a central large pillar 100 and surrounding pillars 102, 104, of smaller dimensions provided in a regular pattern. As may be seen, this pattern includes an iteration of pillars, each of which is formed with the same general shape, but vary with regard to horizontal dimension. This particular complex pattern is an example of a fractal-like pattern that does not include identical alteration in scale between successive recursive iterations. For example, while the pillars 102 are first nanostructures that define a horizontal dimension that is about one third that of the larger pillar 100, which is a microstructure, the pillars 104 are second nanostructures that define a horizontal dimension that is about one half that of the pillars 102.

A pattern that includes structures of different sizes can include larger structures having a cross-sectional dimension formed on a larger scale, e.g., microstructures having a cross-sectional dimension greater than about 500 nanometers in combination with smaller nanostructures. In one embodiment, microstructures of a complex nanotopography can have a cross-sectional dimension between about 500 nanometers and about 10 micrometers, between about 600 nanometers and about 1.5 micrometers, or between about 650 nanometers and about 1.2 micrometers. For example, the complex nanotopography of FIG. 4 includes micro-sized pillars 100 having a cross sectional dimension of about 1.2 micrometers.

When a pattern includes one or more larger microstructures, for instance, having a cross-sectional dimension greater than about 500 nanometers, determined either as the average cross sectional dimension of the structure or as the largest cross sectional dimension of the structure, the complex nanotopography will also include nanostructures, e.g., first nanostructures, second nanostructures of a different size and/or shape, etc. For example, pillars 102 of the complex nanotopography of FIG. 4 have a cross-sectional dimension of about 400 nanometers, and pillars 104 have a cross-sectional dimension of about 200 nanometers.

A nanotopography can be formed of any number of different elements. For instance, a pattern of elements can include two different elements, three different elements, an example of which is illustrated in FIG. 4, four different elements, or more. The relative proportions of the recurrence of each different element can also vary. In one embodiment, the smallest elements of a pattern will be present in larger numbers than the larger elements. For instance in the pattern of FIG. 4, there are eight pillars 104 for each pillar 102, and there are eight pillars 102 for the central large pillar 100. As elements increase in size, there can generally be fewer recurrences of the element in the nanotopography. By way of example, a first element that is about 0.5 times, for instance between about 0.3 times and about 0.7 times in cross-sectional dimension as a second, larger element can be present in the topography about five times or more than the second element. A first element that is approximately 0.25 times, or between about 0.15 times and about 0.3 times in cross-sectional dimension as a second, larger element can be present in the topography about 10 times or more than the second element.

The spacing of individual elements can also vary. For instance, center-to-center spacing of individual structures can be between about 50 nanometers and about 1 micrometer, for instance between about 100 nanometers and about 500 nanometers. For example, center-to-center spacing between structures can be on a nano-sized scale. For instance, when considering the spacing of nano-sized structures, the center-to-center spacing of the structures can be less than about 500 nanometers. This is not a requirement of a topography, however, and individual structures can be farther apart. The center-to-center spacing of structures can vary depending upon the size of the structures. For example, the ratio of the average of the cross-sectional dimensions of two adjacent structures to the center-to-center spacing between those two structures can be between about 1:1 (e.g., touching) and about 1:4, between about 1:1.5 and about 1:3.5, or between about 1:2 and about 1:3. For instance, the center to center spacing can be approximately double the average of the cross-sectional dimensions of two adjacent structures. In one embodiment, two adjacent structures each having a cross-sectional dimension of about 200 nanometers can have a center-to-center spacing of about 400 nanometers. Thus, the ratio of the average of the diameters to the center-to-center spacing in this case is 1:2.

Structure spacing can be the same, i.e., equidistant, or can vary for structures in a pattern. For instance, the smallest structures of a pattern can be spaced apart by a first distance, and the spacing between these smallest structures and a larger structure of the pattern or between two larger structures of the pattern can be the same or different as this first distance.

For example, in the pattern of FIG. 4, the smallest structures 104 have a center-to-center spacing of about 200 nanometers. The distance between the larger pillars 102 and each surrounding pillar 104 is less, about 100 nanometers. The distance between the largest pillar 100 and each surrounding pillar 104 is also less than the center-to-center spacing between two smallest pillars 104, about 100 nanometers. Of course, this is not a requirement, and all structures can be equidistant from one another or any variation in distances. In one embodiment, different structures can be in contact with one another, for instance atop one another, as discussed further below, or adjacent one another and in contact with one another.

Structures of a topography may all be formed to the same height, generally between about 10 nanometers and about 1 micrometer, but this is not a requirement, and individual structures of a pattern may vary in size in one, two, or three dimensions. In one embodiment, some or all of the structures of a topography can have a height of less than about 20 micrometers, less than about 10 micrometers, or less than about 1 micrometer, for instance less than about 750 nanometers, less than about 680 nanometers, or less than about 500 nanometers. For instance the structures can have a height between about 50 nanometers and about 20 micrometers or between about 100 nanometers and about 700 nanometers. For example, nanostructures or microstructures can have a height between about 20 nm and about 500 nm, between about 30 nm and about 300 nm, or between about 100 nm and about 200 nm, though it should be understood that structures may be nano-sized in a cross sectional dimension and may have a height that may be measured on a micro-sized scale, for instance greater than about 500 nm. Micro-sized structures can have a height that is the same or different from nano-sized structures of the same pattern. For instance, micro-sized structures can have a height of between about 500 nanometers and about 20 micrometers, or between about 1 micrometer and about 10 micrometers, in another embodiment. Micro-sized structures may also have a cross sectional dimension on a micro-scale greater than about 500 nm, and may have a height that is on a nano-sized scale of less than about 500 nm.

The aspect ratio of the structures (the ratio of the height of a structure to the cross sectional dimension of the structure) can be between about 0.15 and about 30, between about 0.2 and about 5, between about 0.5 and about 3.5, or between about 1 and about 2.5. For instance, the aspect ratio of the nanostructures may fall within these ranges.

Figure 5:
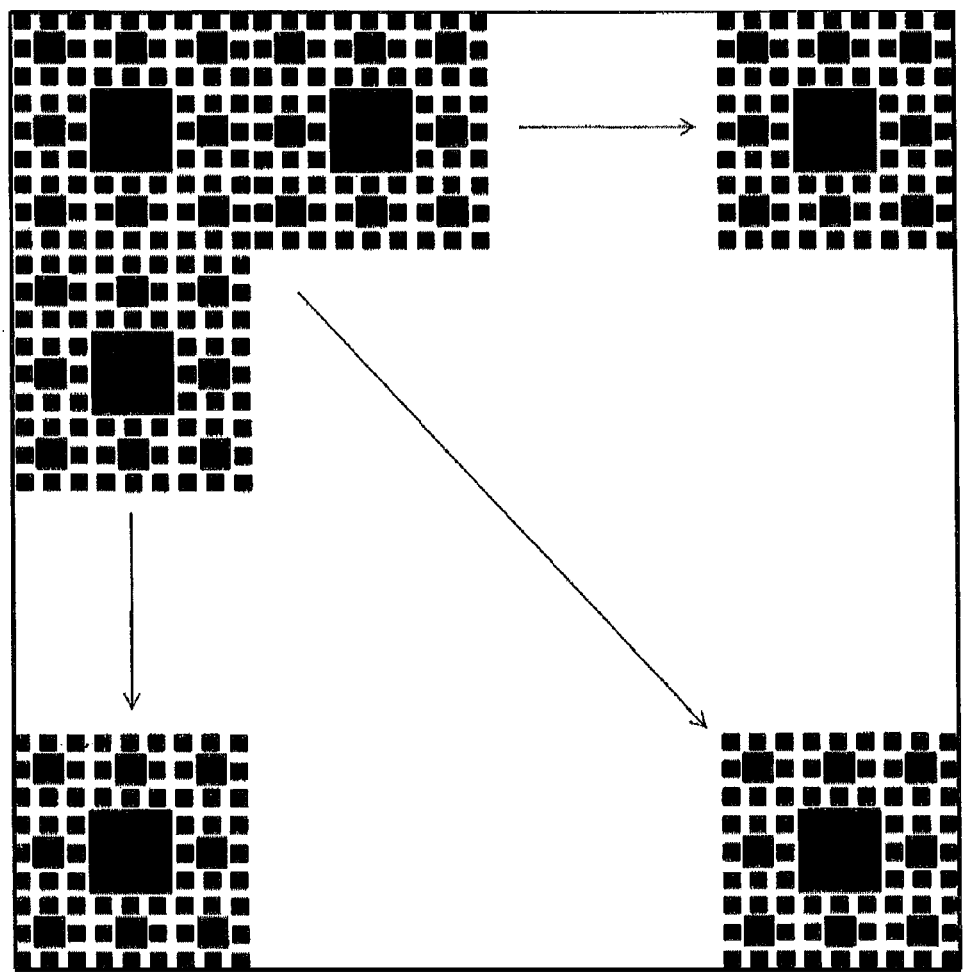
FIG. 5 illustrates a pattern including multiple iterations of the complex pattern of FIG. 4.

The device surface may include a single instance of a pattern, as shown in FIG. 4, or may include multiple iterations of the same or different patterns. For example, FIG. 5 illustrates a surface pattern including the pattern of FIG. 4 in multiple iterations over a surface.

The formation of nanotopography on a surface may increase the surface area without a corresponding increase in volume. Increase in the surface area to volume ratio is believed to improve the interaction of a surface with surrounding biological materials. For instance, increase in the surface area to volume ratio is believed to encourage mechanical interaction between the nanotopography and surrounding proteins, e.g., extracellular matrix (ECM) proteins and/or plasma membrane proteins.

In general, the surface area to volume ratio of the device may be greater than about 10,000 $cm^{-1}$, greater than about 150,000 $cm^{-1}$, or greater than about 750,000 $cm^{-1}$. Determination of the surface area to volume ratio may be carried out according to any standard methodology as is known in the art. For instance, the specific surface area of a surface may be obtained by the physical gas adsorption method (B.E.T. method) with nitrogen as the adsorption gas, as is generally known in the art and described by *Brunauer, Emmet, and Teller* (J. Amer. Chem. Soc., vol. 60, February, 1938, pp. 309-319), incorporated herein by reference. The BET surface area can be less than about 5 $m^2/g$, in one embodiment, for instance between about 0.1 $m^2/g$ and about 4.5 $m^2/g$, or between about 0.5 $m^2/g$ and about 3.5 $m^2/g$. Values for surface area and volume may also be estimated from the geometry of molds used to form a surface, according to standard geometric calculations. For example, the volume can be estimated according to the calculated volume for each pattern element and the total number of pattern elements in a given area, e.g., over the surface of a single microneedle.

For a device that defines a complex pattern nanotopography at a surface, the nanotopography may be characterized through determination of the fractal dimension of the pattern. The fractal dimension is a statistical quantity that gives an indication of how completely a fractal appears to fill space as the recursive iterations continue to smaller and smaller scale. The fractal dimension of a two dimensional structure may be represented as:

$$D = \frac{\log N(e)}{\log(e)}$$

where N(e) is the number of self-similar structures needed to cover the whole object when the object is reduced by 1/e in each spatial direction.

Figure 6:
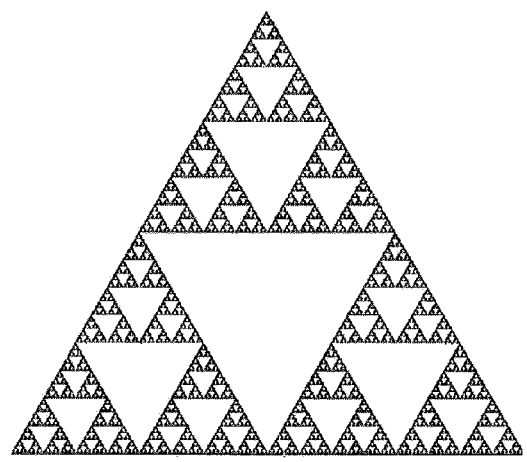
FIG. 6 illustrates a Sierpinski triangle fractal.

For example, when considering the two dimensional fractal known as the Sierpenski triangle illustrated in FIG. 6, in which the mid-points of the three sides of an equilateral triangle are connected and the resulting inner triangle is removed, the fractal dimension is calculated as follows:

$$D = \frac{\log N(e)}{\log(e)}$$

$$D = \frac{\log 3}{\log 2}$$

$$D \approx 1.585$$

Thus, the Sierpenski triangle fractal exhibits an increase in line length over the initial two dimensional equilateral triangle. Additionally, this increase in line length is not accompanied by a corresponding increase in area.

The fractal dimension of the pattern illustrated in FIG. 4 is approximately 1.84. In one embodiment, nanotopography of a surface of the device may exhibit a fractal dimension of greater than about 1, for instance between about 1.2 and about 5, between about 1.5 and about 3, or between about 1.5 and about 2.5.

Figure 7:
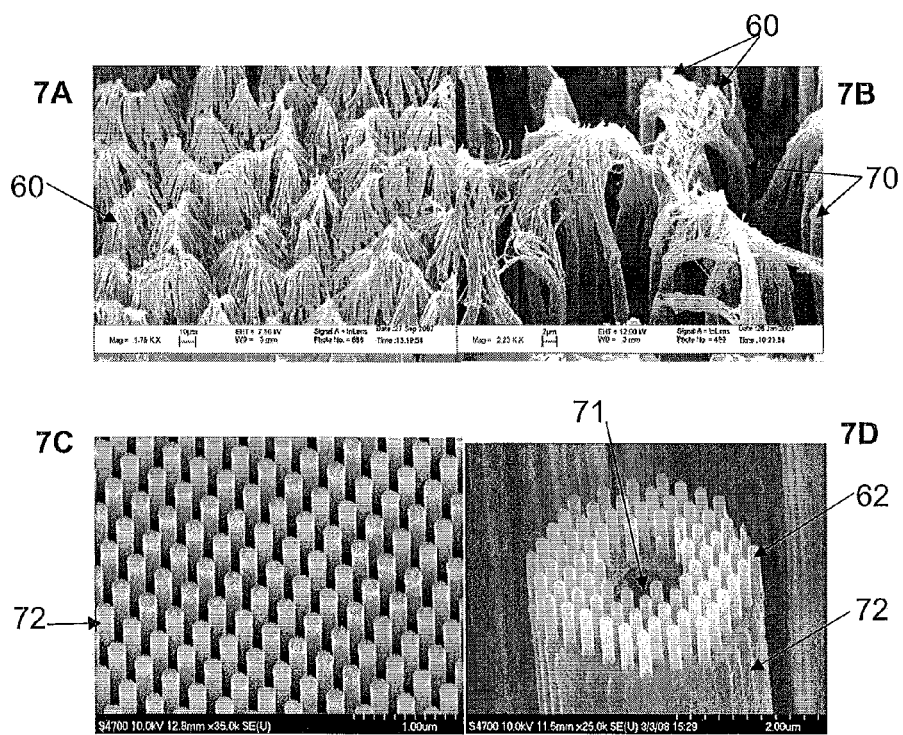
FIGS. 7A-7D illustrate complex fractal and fractal-like nanotopographies.

FIGS. 7A and 7B illustrate increasing magnification images of another example of a complex nanotopography. The nanotopography of FIGS. 7A and 7B includes an array of fibrous-like pillars 70 located on a substrate. At the distal end of each individual pillar, the pillar splits into multiple smaller fibers 60. At the distal end of each of these smaller fibers 60, each fiber splits again into multiple filaments (not visible in FIGS. 7A and 7B). Structures formed on a surface that have an aspect ratio greater than about 1 may be flexible, as are the structures illustrated in FIGS. 7A and 7B, or may be stiff.

FIGS. 7C and 7D illustrate another example of a complex nanotopography. In this embodiment, a plurality of pillars 72 each including an annular hollow therethrough 71 are formed on a substrate. At the distal end of each hollow pillar, a plurality of smaller pillars 62 is formed. As may be seen, the pillars of FIGS. 7C and 7D maintain their stiffness and upright orientation. Additionally, and in contrast to previous patterns, the smaller pillars 62 of this embodiment differ in shape from the larger pillars 72. Specifically, the smaller pillars 62 are not hollow, but are solid. Thus, nanotopography including structures formed to a different scale need not have all structures formed with the same shape, and structures may vary in both size and shape from the structures of a different scale.

Figure 8:
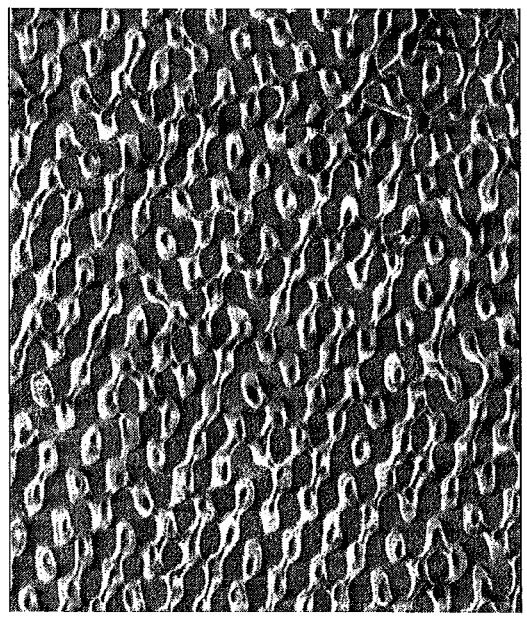
FIG. 8 illustrates another complex pattern that may be formed on a microneedle surface.

FIG. 8 illustrates another pattern including nano-sized structures as may be formed on the device surface. As may be seen, in this embodiment, individual pattern structures may be formed at the same general size, but with different orientations and shapes from one another.

In addition to or alternative to those methods mentioned above, a surface may be characterized by other methods including, without limitation, surface roughness, elastic modulus, and surface energy.

Methods for determining the surface roughness are generally known in the art. For instance, an atomic force microscope process in contact or non-contact mode may be utilized according to standard practice to determine the surface roughness of a material. Surface roughness that may be utilized to characterize a microneedle can include the average roughness ($R_A$), the root mean square roughness, the skewness, and/or the kurtosis. In general, the average surface roughness (i.e., the arithmetical mean height of the surface are roughness parameter as defined in the ISO 25178 series) of a surface defining a fabricated nanotopography thereon may be less than about 200 nanometers, less than about 190 nanometers, less than about 100 nanometers, or less than about 50 nanometers. For instance, the average surface roughness may be between about 10 nanometers and about 200 nanometers, or between about 50 nanometers and about 190 nanometers.

The device may be characterized by the elastic modulus of the nanopatterned surface, for instance by the change in elastic modulus upon the addition of a nanotopography to a surface. In general, the addition of a plurality of structures forming nanotopography on a surface can decrease the elastic modulus of a material, as the addition of nano-sized structures on a surface will lead to a reduction in continuity of the surface and a related change in surface area. As compared to a similar surface formed according to the same process and of the same materials, but for a pattern of nanotopography on the surface, the device including nanotopography thereon can exhibit a decrease in elastic modulus of between about 35% and about 99%, for instance between about 50% and about 99%, or between about 75% and about 80%. By way of example, the effective compression modulus of a nanopatterned surface can be less than about 50 MPa, or less than about 20 MPa. In one embodiment the effective compression modulus can be between about 0.2 MPa and about 50 MPa, between about 5 MPa and about 35 MPa, or between about 10 MPa and about 20 MPa. The effective shear modulus can be less than about 320 MPa, or less than about 220 MPa. For instance, the effective shear modulus can be between about 4 MPa and about 320 MPa, or between about 50 MPa and about 250 MPa, in one embodiment.

The device including nanotopography thereon may also exhibit an increase in surface energy as compared to a similar microneedle that does not have a surface defining a pattern of nanotopography thereon. For instance, a microneedle including a nanotopography formed thereon can exhibit an increase in surface energy as compared to a similar microneedle of the same materials and formed according to the same methods, but for the inclusion of a pattern of nanotopography on a surface. For instance, the water contact angle of a surface including a nanotopography thereon can be greater than about 80°, greater than about 90°, greater than about 100°, or greater than about 110°. For example, the water contact angle of a surface can be between about 80° and about 150°, between about 90° and about 130°, or between about 100° and about 120°, in one embodiment.

Figures 9A, 9B:
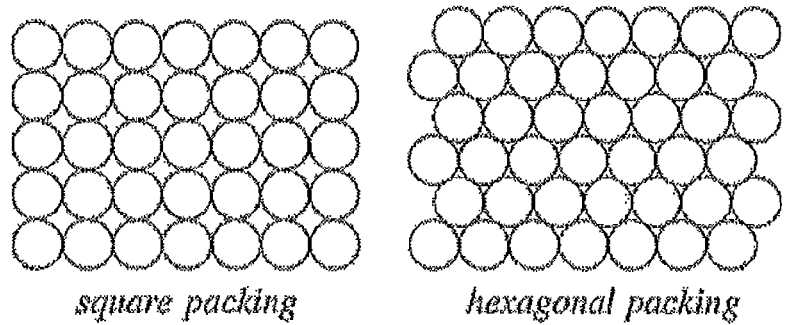
FIG. 9 illustrates exemplary packing densities as may be utilized for nano-sized structures as described herein including a square packing design (FIG. 9A), a hexagonal packing design (FIG. 9B), and a circle packing design (FIG. 9C).
Figure 9C:
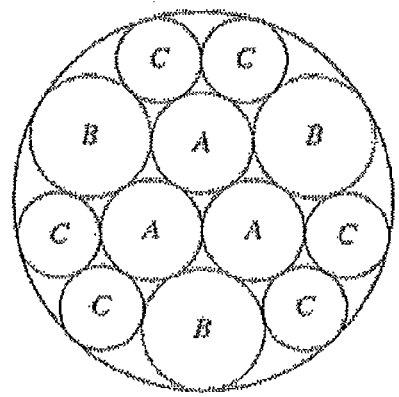

When forming nanostructures on the surface of the device, the packing density of the structures may be maximized. For instance, square packing (FIG. 9A), hexagonal packing (FIG. 9B), or some variation thereof may be utilized to pattern the elements on a substrate. When designing a pattern in which various sized elements of cross sectional areas A, B, and C are adjacent to one another on a substrate, circle packing as indicated in FIG. 9C may be utilized. Of course, variations in packing density and determination of associated alterations in characteristics of a surface are well within the abilities of one of skill in the art.

The device including a fabricated nanotopography on a surface of the device may be formed according to a single-step process. Alternatively, a multi-step process may be used, in which a pattern of nanostructures are fabricated on a pre-formed surface. For example, an array of microneedles may be first formed and then a random or non-random pattern of nanostructures may be fabricated on the surface of the formed microneedles. In either the single-step or two-step process, structures may be fabricated on a surface or on a mold surface according to any suitable nanotopography fabrication method including, without limitation, nanoimprinting, injection molding, lithography, embossing molding, and so forth.

In general, an array of microneedles may be formed according to any standard microfabrication technique including, without limitation, lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation).

Lithography techniques, including photolithography, e-beam lithography, X-ray lithography, and so forth may be utilized for primary pattern definition and formation of a master die. Replication may then be carried out to form the device including an array of microneedles. Common replication methods include, without limitation, solvent-assisted micromolding and casting, embossing molding, injection molding, and so forth. Self-assembly technologies including phase-separated block copolymer, polymer demixing and colloidal lithography techniques may also be utilized in forming a nanotopography on a surface.

Combinations of methods may be used, as is known. For instance, substrates patterned with colloids may be exposed to reactive ion etching (RIE, also known as dry etching) so as to refine the characteristics of a fabricated nanostructure such as nanopillar diameter, profile, height, pitch, and so forth. Wet etching may also be employed to produce alternative profiles for fabricated nanostructures initially formed according to a different process, e.g., polymer demixing techniques. Structure diameter, shape, and pitch may be controlled via selection of appropriate materials and methods.

Other methods as may be utilized in forming a microneedle including a fabricated nanotopography on a surface include nanoimprint lithography methods utilizing ultra-high precision laser machining techniques, examples of which have been described by Hunt, et al. (U.S. Pat. No. 6,995,336) and Guo, et al. (U.S. Pat. No. 7,374,864), both of which are incorporated herein by reference. Nanoimprint lithography is a nano-scale lithography technique in which a hybrid mold is utilized which acts as both a nanoimprint lithography mold and a photolithography mask. A schematic of a nanoimprint lithography technique is illustrated in FIGS. 10A-10C. During fabrication, a hybrid mold 30 imprints into a substrate 32 via applied pressure to form features (e.g., microneedles defining nanotopography) on a resist layer (FIG. 10A). In general, the surface of the substrate 32 may be heated prior to engagement with the mold 30 to a temperature above its glass transition temperature ($T_g$). While the hybrid mold 30 is engaged with the substrate 32, a flow of viscous polymer may be forced into the mold cavities to form features 34 (FIG. 10B). The mold and substrate may then be exposed to ultraviolet light. The hybrid mold is generally transmissive to UV radiation save for certain obstructed areas. Thus, the UV radiation passes through transmissive portions and into the resist layer. Pressure is maintained during cooling of the mold and substrate. The hybrid mold 30 is then removed from the cooled substrate 32 at a temperature below $T_g$ of the substrate and polymer (FIG. 10C).

To facilitate the release of the nanoimprinted substrate 32 including fabricated features 34 from the mold 30, as depicted in FIG. 10C, it is advantageous to treat the mold 30 with a low energy coating to reduce the adhesion with the substrate 32, as a lower surface energy of the mold 30 and the resulting greater surface energy difference between the mold 30, substrate 32, and polymer may ease the release between the materials. By way of example, a silicon mold coating may be used such as trideca-(1,1,2,2-tetrahydro)-octytrichloro silane ($F_{13}$-TCS).

Structures may also be formed according to chemical addition processes. For instance, film deposition, sputtering, chemical vapor deposition (CVD); epitaxy (vapor phase, liquid phase, and molecular beam), electroplating, and so forth can be utilized for building structures on a surface. Self-assembled monolayer processes as are known in the art can be utilized to form a pattern of structures on a surface.

The surface of a transdermal delivery device can be further functionalized for improved interaction with tissues or individual cells during use. For instance, one or more biomolecules such as polynucleotides, polypeptides, entire proteins, polysaccharides, and the like can be bound to a structured surface prior to use.

In some embodiments, a surface including structures formed thereon can already contain suitable reactivity such that additional desired functionality may spontaneously attach to the surface with no pretreatment of the surface necessary. However, in other embodiments, pretreatment of the structured surface prior to attachment of the desired compound may be carried out. For instance, reactivity of a structure surface may be increased through addition or creation of amine, carboxylic acid, hydroxy, aldehyde, thiol, or ester groups on the surface. In one representative embodiment, a microneedle surface including a pattern of nanostructures formed thereon may be aminated through contact with an amine-containing compound such as 3-aminopropyltriethoxy silane in order to increase the amine functionality of the surface and bind one or more biomolecules to the surface via the added amine functionality.

Materials as may be desirably bound to the surface of a patterned device can include ECM proteins such as laminins, tropoelastin or elastin, Tropocollagen or collagen, fibronectin, and the like. Short polypeptide fragments can be bound to the surface of a patterned device such as an RGD sequence, which is part of the recognition sequence of integrin binding to many ECM proteins. Thus, functionalization of a microneedle surface with RGD can encourage interaction of the device with ECM proteins and further limit foreign body response to the device during use.

The transdermal delivery device may be in the form of a patch that may include various features. For example, the device may include a reservoir, e.g., a vessel, a porous matrix, etc., that may store and agent and provide the agent for delivery. The device may include a reservoir within the device itself. For instance, the device may include a hollow, or multiple pores that may carry one or more agents for delivery. The agent may be released from the device via degradation of a portion or the entire device or via diffusion of the agent from the device.

FIGS. 11A and 11B are perspective views of the device including a reservoir. The device 110 includes a reservoir 112 defined by an impermeable backing layer 114 and a microneedle array 116. The backing layer and the microneedle array 116 are joined together about the outer periphery of the device, as indicated at 118. The impermeable backing layer 114 may be joined by an adhesive, a heat seal or the like. The device 110 also includes a plurality of microneedles 120. A release liner 122 can be removed prior to use of the device to expose microneedles 120.

A formulation including one or more agents may be retained within the reservoir 112. Materials suitable for use as impermeable backing layer 114 can include materials such as polyesters, polyethylene, polypropylene and other synthetic polymers. The material is generally heat or otherwise sealable to the backing layer to provide a barrier to transverse flow of reservoir contents.

Reservoir 112, defined by the space or gap between the impermeable backing layer 114 and the microneedle array 116, provides a storage structure in which to retain the suspension of agents to be administered. The reservoir may be formed from a variety of materials that are compatible with an agent to be contained therein. By way of example, natural and synthetic polymers, metals, ceramics, semiconductor materials, and composites thereof may form the reservoir.

In one embodiment, the reservoir may be attached to the substrate upon which the microneedles are located. According to another embodiment, the reservoir may be separate and removably connectable to the microneedle array or in fluid communication with the microneedle array, for instance via appropriate tubing, leur locks, etc.

The device may include one or a plurality of reservoirs for storing agents to be delivered. For instance, the device may include a single reservoir that stores a single or multiple agent-containing formulation, or the device may include multiple reservoirs, each of which stores one or more agents for delivery to all or a portion of the array of microneedles. Multiple reservoirs may each store a different material that may be combined for delivery. For instance, a first reservoir may contain an agent, e.g., a drug, and a second reservoir may contain a vehicle, e.g., saline. The different agents may be mixed prior to delivery. Mixing may be triggered by any means, including, for example, mechanical disruption (i.e. puncturing, degradation, or breaking), changing the porosity, or electrochemical degradation of the walls or membranes separating the chambers. Multiple reservoirs may contain different active agents for delivery that may be delivered in conjunction with one another or sequentially.

In one embodiment, the reservoir may be in fluid communication with one or more microneedles of the transdermal device, and the microneedles may define a structure (e.g., a central or lateral bore) to allow transport of delivered agents beneath the barrier layer.

In alternative embodiments, a device may include a microneedle assembly and a reservoir assembly with flow prevention between the two prior to use. For instance, a device may include a release member positioned adjacent to both a reservoir and a microneedle array. The release member may be separated from the device prior to use such that during use the reservoir and the microneedle array are in fluid communication with one another. Separation may be accomplished through the partial or complete detachment of the release member. For example, referring to FIGS. 12-17, one embodiment of a release member is shown that is configured to be detached from a transdermal patch to initiate the flow of a drug compound. More particularly, FIGS. 12-17 show a transdermal patch 300 that contains a drug delivery assembly 370 and a microneedle assembly 380. The drug delivery assembly 370 includes a reservoir 306 positioned adjacent to a rate control membrane 308.

The rate control membrane may help slow down the flow rate of the drug compound upon its release. Specifically, fluidic drug compounds passing from the drug reservoir to the microneedle assembly via microfluidic channels may experience a drop in pressure that results in a reduction in flow rate. If this difference is too great, some backpressure may be created that may impede the flow of the compound and potentially overcome the capillary pressure of the fluid through the microfluidic channels. Thus, the use of the rate control membrane may ameliorate this difference in pressure and allow the drug compound to be introduced into the microneedle at a more controlled flow rate. The particular materials, thickness, etc. of the rate control membrane may vary based on multiple factors, such as the viscosity of the drug compound, the desired delivery time, etc.

The rate control membrane may be fabricated from permeable, semi-permeable or microporous materials that are known in the art to control the rate of drug compounds and having permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. Such membrane materials are also described in more detail in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, 5,364,630, and 6,375,978, which are incorporated in their entirety herein by reference for all relevant purposes. A particularly suitable membrane material is available from Lohmann Therapie-Systeme.

Referring to FIGS. 12-13, although optional, the assembly 370 also contains an adhesive layer 304 that is positioned adjacent to the reservoir 306. The microneedle assembly 380 likewise includes a support 312 from which extends a plurality of microneedles 330 having channels 331, such as described above. The layers of the drug delivery assembly 370 and/or the microneedle assembly 380 may be attached together if desired using any known bonding technique, such as through adhesive bonding, thermal bonding, ultrasonic bonding, etc.

Regardless of the particular configuration employed, the patch 300 also contains a release member 310 that is positioned between the drug delivery assembly 370 and the microneedle assembly 380. While the release member 310 may optionally be bonded to the adjacent support 312 and/or rate control membrane 308, it is typically desired that it is only lightly bonded, if at all, so that the release member 310 may be easily withdrawn from the patch 300. If desired, the release member 310 may also contain a tab portion 371 (FIGS. 12-13) that extends at least partly beyond the perimeter of the patch 300 to facilitate the ability of a user to grab onto the member and pull it in the desired direction. In its "inactive" configuration as shown in FIGS. 12-13, the drug delivery assembly 370 of the patch 300 securely retains a drug compound 307 so that it does not flow to any significant extent into the microneedles 330. The patch may be "activated" by simply applying a force to the release member so that it is detached from the patch.

Referring to FIGS. 14-15, one embodiment for activating the patch 300 is shown in which the release member 310 is pulled in a longitudinal direction. The entire release member 310 may be removed as shown in FIGS. 16-17, or it may simply be partially detached as shown in FIGS. 14-15. In either case, however, the seal previously formed between the release member 310 and the aperture (not shown) of the support 312 is broken. In this manner, a drug compound 107 may begin to flow from the drug delivery assembly 170 and into the channels 131 of the microneedles 130 via the support 112. An exemplary illustration of how the drug compound 307 flows from the reservoir 306 and into the channels 331 is shown in FIGS. 16-17. Notably, the flow of the drug compound 307 is passively initiated and does not require any active displacement mechanisms (e.g., pumps).

In the embodiments shown in FIGS. 12-17, the detachment of the release member immediately initiates the flow of the drug compound to the microneedles because the drug delivery assembly is already disposed in fluid communication with the microneedle assembly. In certain embodiments, however, it may be desired to provide the user with a greater degree of control over the timing of the release of the drug compound. This may be accomplished by using a patch configuration in which the microneedle assembly is not initially in fluid communication with the drug delivery assembly. When it is desired to use the patch, the user may physically manipulate the two separate assemblies into fluid communication. The release member may be separated either before or after such physical manipulation occurs.

Referring to FIGS. 18-23, for example, one particular embodiment of a patch 200 is shown. FIGS. 18-19 illustrate the patch 200 before use, and shows a first section 250 formed by a microneedle assembly 280 and a second section 260 formed by a drug delivery assembly 270. The drug delivery assembly 270 includes a reservoir 206 positioned adjacent to a rate control membrane 208 as described above. Although optional, the assembly 270 also contains an adhesive layer 204 that is positioned adjacent to the reservoir 206. The microneedle assembly 280 likewise includes a support 212 from which extends a plurality of microneedles 230 having channels 231, such as described above.

In this embodiment, the support 212 and the rate control membrane 208 are initially positioned horizontally adjacent to each other, and a release member 210 extends over the support 212 and the rate control member 208. In this particular embodiment, it is generally desired that the release member 210 is releasably attached to the support 212 and the rate control membrane 208 with an adhesive (e.g., pressure-sensitive adhesive). In its "inactive" configuration as shown in FIGS. 18-19, the drug delivery assembly 270 of the patch 200 securely retains a drug compound 207 so that it does not flow to any significant extent into the microneedles 230. When it is desired to "activate" the patch, the release member 210 may be peeled away and removed, such as illustrated in FIGS. 20-21, to break the seal previously formed between the release member 210 and the aperture (not shown) of the support 212. Thereafter, the second section 260 may be folded about a fold line "F" as shown by the directional arrow in FIG. 22 so that the rate control member 208 is positioned vertically adjacent to the support 212 and in fluid communication therewith. Alternatively, the first section 250 may be folded. Regardless, folding of the sections 250 and/or 260 initiates the flow of a drug compound 207 from the drug delivery assembly 270 and into the channels 231 of the microneedles 230 via the support 212 (See FIG. 23).

The device may deliver an agent at a rate so as to be therapeutically useful. In accord with this goal, a transdermal device may include a housing with microelectronics and other micro-machined structures to control the rate of delivery either according to a preprogrammed schedule or through active interface with the patient, a healthcare professional, or a biosensor. The device may include a material at a surface having a predetermined degradation rate, so as to control release of an agent contained within the device. A delivery rate may be controlled by manipulating a variety of factors, including the characteristics of the formulation to be delivered (e.g., viscosity, electric charge, and/or chemical composition); the dimensions of each device (e.g., outer diameter and the volume of any openings); the number of microneedles on a transdermal patch; the number of individual devices in a carrier matrix; the application of a driving force (e.g., a concentration gradient, a voltage gradient, a pressure gradient); the use of a valve; and so forth.

Transportation of agents through the device may be controlled or monitored using, for example, various combinations of valves, pumps, sensors, actuators, and microprocessors. These components may be produced using standard manufacturing or microfabrication techniques. Actuators that may be useful with the device may include micropumps, microvalves, and positioners. For instance, a microprocessor may be programmed to control a pump or valve, thereby controlling the rate of delivery.

Flow of an agent through the device may occur based on diffusion or capillary action, or may be induced using conventional mechanical pumps or nonmechanical driving forces, such as electroosmosis or electrophoresis, or convection. For example, in electroosmosis, electrodes are positioned on a biological surface (e.g., the skin surface), a microneedle, and/or a substrate adjacent a microneedle, to create a convective flow which carries oppositely charged ionic species and/or neutral molecules toward or into the delivery site.

Flow of an agent may be manipulated by selection of the material forming the microneedle surface. For example, one or more large grooves adjacent the microneedle surface of the device may be used to direct the passage of drug, particularly in a liquid state. Alternatively, the physical surface properties of the device may be manipulated to either promote or inhibit transport of material along the surface, such as by controlling hydrophilicity or hydrophobicity.

The flow of an agent may be regulated using valves or gates as is known in the art. Valves may be repeatedly opened and closed, or they may be single-use valves. For example, a breakable barrier or one-way gate may be installed in the device between a reservoir and the patterned surface. When ready to use, the barrier may be broken or gate opened to permit flow through to the microneedle surface. Other valves or gates used in the device may be activated thermally, electrochemically, mechanically, or magnetically to selectively initiate, modulate, or stop the flow of molecules through the device. In one embodiment, flow is controlled by using a rate-limiting membrane as a "valve."

In general, any agent delivery control system, including reservoirs, flow control systems, sensing systems, and so forth as are known in the art may be incorporated with devices. By way of example, U.S. Pat. Nos. 7,250,037, 7,315,758, 7,429,258, 7,582,069, and 7,611,481 describe reservoir and control systems as may be incorporated in devices.

The subject matter may be better understood with reference to the Examples, presented below.

Example 1

Several different molds were prepared using photolithography techniques similar to those employed in the design and manufacture of electrical circuits. Individual process steps are generally known in the art and have been described Initially, silicon substrates were prepared by cleaning with acetone, methanol, and isopropyl alcohol, and then coated with a 258 nanometer (nm) layer of silicon dioxide according to a chemical vapor deposition process.

A pattern was then formed on each substrate via an electron beam lithography patterning process as is known in the art using a JEOL JBX-9300FS EBL system. The processing conditions were as follows:

Beam current=11 nA
Acceleration voltage=100 kV
Shot pitch=14 nm
Dose=260 μC/cm$^2$
Resist=ZEP520A, ~330 nm thickness
Developer=n-amyl acetate
Development=2 min. immersion, followed by 30 sec. isopropyl alcohol rinse.

A silicon dioxide etch was then carried out with an STS Advanced Oxide Etch (AOE). Etch time was 50 seconds utilizing 55 standard cubic centimeters per minute (sccm) He, 22 sccm CF$_4$, 20 sccm C$_4$F$_8$ at 4 mTorr, 400 W coil, 200 W RIE and a DC Bias of 404-411 V.

Following, a silicon etch was carried out with an STS silicon oxide etch (SOE). Etch time was 2 minutes utilizing 20 sccm Cl$_2$ and 5 sccm Ar at 5 mTorr, 600 W coil, 50 W RIE and a DC Bias of 96-102 V. The silicon etch depth was 500 nanometers.

A buffered oxide etchant (BOE) was used for remaining oxide removal that included a three minute BOE immersion followed by a deionized water rinse.

An Obducat NIL-Eitre®6 nanoimprinter was used to form nanopatterns on a variety of polymer substrates. External water was used as coolant. The UV module utilized a single pulsed lamp at a wave length of between 200 and 1000 nanometers at 1.8 W/cm$^2$. A UV filter of 250-400 nanometers was used. The exposure area was 6 inches with a maximum temperature of 200° C. and 80 Bar. The nanoimprinter included a semi-automatic separation unit and automatic controlled demolding.

To facilitate the release of the nanoimprinted films from the molds, the molds were treated with Trideca-(1,1,2,2-tetrahydro)-octytrichlorosilane ($F_{13}$-TCS). To treat a mold, the silicon mold was first cleaned with a wash of acetone, methanol, and isopropyl alcohol and dried with a nitrogen gas. A Petri dish was placed on a hot plate in a nitrogen atmosphere and 1-5 ml of the $F_{13}$-TCS was added to the Petri dish. A silicon mold was placed in the Petri dish and covered for 10-15 minutes to allow the $F_{13}$-TCS vapor to wet out the silicon mold prior to removal of the mold.

Five different polymers as given in Table 1, below, were utilized to form various nanotopography designs.

TABLE 1

| Polymer | Glass Transition Temperature, $T_g$ (K) | Tensile Modulus (MPa) | Surface Tension (mN/m) @20° C. |
|---|---|---|---|
| Polyethylene | 140-170 | 100-300 | 30 |
| Polypropylene | 280 | 1,389 | 21 |
| PMMA | 322 | 3,100 | 41 |
| Polystyrene | 373 | 3,300 | 40 |
| Polycarbonate | 423 | 2,340 | 43 |

Figure 24A:
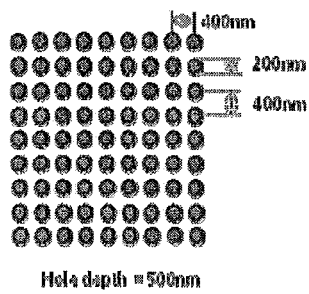
Figure 24A:
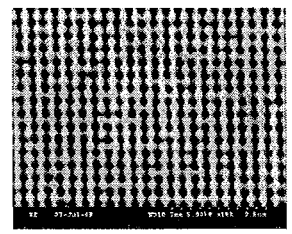
Figure 24B:
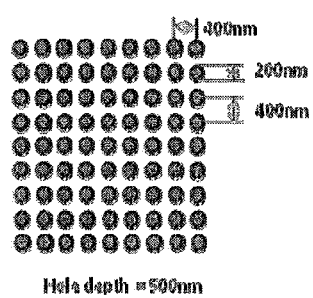
Figure 24B:
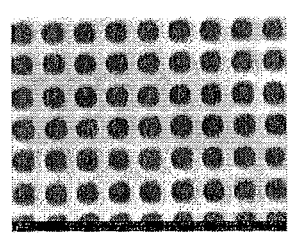
Figure 24C:
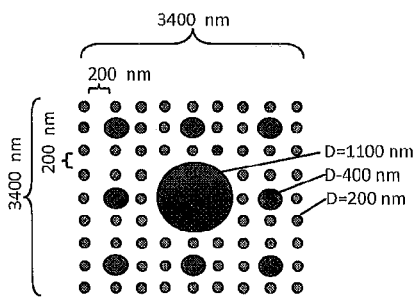
Figure 24C:
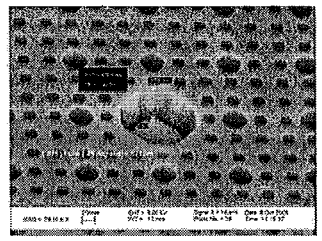
Figure 24D:
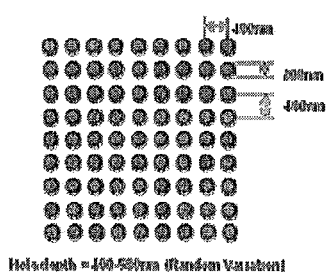
Figure 24D:
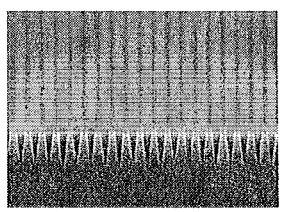

Several different nanotopography patterns were formed, schematic representations of which are illustrated in FIGS. 24A-24D. The nanotopography pattern illustrated in FIG. 24E was a surface of a flat substrate purchased from NTT Advanced Technology of Tokyo, Japan. The patterns were designated DN1 (FIG. 24A), DN2 (FIG. 24B), DN3 (FIG. 24C), DN4 (FIG. 24D) and NTTAT2 (FIG. 24E). SEM images of the molds are shown in FIGS. 24A, 24B, and 24C, and images of the films are shown in FIGS. 24D and 24E. FIG. 8 illustrates a nanopatterned film formed by use of the mold of FIG. 24A (DN1). In this particular film, the polymer features were drawn by temperature variation as previously discussed. The surface roughness of the pattern of FIG. 24E was found to be 34 nanometers.

The pattern illustrated in FIGS. 7C and 7D was also formed according to this nanoimprinting process. This pattern included the pillars 72 and pillars 62, as illustrated. Larger pillars 72 were formed with a 3.5 micrometer (μm) diameter and 30 μm heights with center-to-center spacing of 6.8 μm. Pillars 62 were 500 nanometers in height and 200 nanometers in diameter and a center-to-center spacing of 250 nanometers.

The nanoimprinting process conditions used with polypropylene films are provided below in Table 2.

TABLE 2

| Time (s) | Temperature (C.) | Pressure (Bar) |
|---|---|---|
| 10 | 50 | 10 |
| 10 | 75 | 20 |
| 10 | 100 | 30 |
| 420 | 160 | 40 |
| 180 | 100 | 40 |
| 180 | 50 | 40 |
| 180 | 25 | 40 |

Example 2

Films were formed as described above in Example 1 including various different patterns and formed of either polystyrene (PS) or polypropylene (PP). The underlying substrate varied in thickness. Patterns utilized were DN2, DN3, or DN4 utilizing formation processes as described in Example 1. The pattern molds were varied with regard to hole depth and feature spacing to form a variety of differently-sized features having the designated patterns. Sample no. 8 (designated BB1) was formed by use of a 0.6 μm millipore polycarbonate filter as a mold. A 25 μm polypropylene film was laid over the top of the filter and was then heated to melt such that the polypropylene could flow into the pores of the filter. The mold was then cooled and the polycarbonate mold dissolved by use of a methylene chloride solvent.

SEMs of the formed films are shown in FIGS. 25-33 and the characteristics of the formed films are summarized in Table 3, below.

TABLE 3

| Sample No. | Fig. | Pattern | Material | Film thickness (μm) | Pattern Feature[1] | Cross Sectional Dimension[2] | Feature height[3] | Aspect Ratio | Surface Roughness (nm) | Fractal Dimension | Water Contact Angle |
|---|---|---|---|---|---|---|---|---|---|---|---|
| 1 | 25 | DN3 | PS | 75 | A | 1100 nm | 520 nm | 0.47 | 150 | 2.0 | 100° |
|  |  |  |  |  | B | 400 nm | 560 nm | 1.4 |  |  |  |
|  |  |  |  |  | C | 200 nm | 680 nm | 3.4 |  |  |  |
| 2 | 26A, 26B | DN2 | PP | 5.0 | n/a | 200 nm | 100 nm | 0.5 | 16 | 2.15 | 91° |
| 3 | 27 | DN2 | PS | 75 | n/a | 200 nm | 1.0 μm | 5 | 64 | 2.2 | 110° |
| 4 | 28 | DN2 | PP | 25.4 | n/a | 200 nm | 300 nm | 1.5 | 38 | 1.94 | 118° |
| 5 | 29 | DN3 | PS | 75 | A | 1100 nm | 570 nm | 0.52 | 21.1 | 1.98 | 100° |
|  |  |  |  |  | B | 400 nm | 635 nm | 1.6 |  |  |  |
|  |  |  |  |  | C | 200 nm | — | — |  |  |  |
| 6 | 30 | DN4 | PS | 75 | n/a | 200 nm | — | — | 30.6 | 2.04 | 80° |
| 7 | 31 | DN4 | PP | 25.4 | n/a | 200 nm | — | — | 21.4 | 2.07 | 112° |
| 8 | 32 | BB1 | PP | 25.4 | n/a | 600 nm | 18 μm | 30 | 820 | 2.17 | 110° |
| 9 | 33 | DN3 | PP | 5 | A | 1100 nm | 165 nm | 0.15 | 50 | 2.13 | — |
|  |  |  |  |  | B | 400 nm | 80 nm | 0.2 |  |  |  |
|  |  |  |  |  | C | 200 nm | 34 nm | 0.17 |  |  |  |

[1]Pattern Features as shown on the figures.
[2]Cross sectional dimension values were derived from the mold and equated as an approximation of the maximum dimension of the structures, although it should be understood that the actual dimension of any given individual structure may vary slightly as may be seen in the figures.
[3]Feature heights are provided as the average of several individually determined feature heights.

For each sample AFM was utilized to characterize the film. Characterizations included formation of scanning electron micrograph (SEM), determination of surface roughness, determination of maximum measured feature height, and determination of fractal dimension.

The atomic force microscopy (AFM) probe utilized was a series 16 silicon probe and cantilever available from µMasch. The cantilever had a resonant frequency of 170 kHz, a spring constant of 40 N/m, a length of 230±5 µm, a width of 40±3 µm, and a thickness of 7.0±0.5 µm. The probe tip was an n-type phosphorous-doped silicon probe, with a typical probe tip radius of 10 nanometers, a full tip cone angle of 40°, a total tip height of 20-25 µm, and a bulk resistivity 0.01-0.05 ohm-cm.

The surface roughness value given in Table 4 is the arithmetical mean height of the surface area roughness parameter as defined in the ISO 25178 series.

The Fractal Dimension was calculated for the different angles by analyzing the Fourier amplitude spectrum; for different angles the amplitude Fourier profile was extracted and the logarithm of the frequency and amplitude coordinates calculated. The fractal dimension, D, for each direction is then calculated as $$D=(6+s)/2,$$

where s is the (negative) slope of the log–log curves. The reported fractal dimension is the average for all directions.

The fractal dimension can also be evaluated from 2D Fourier spectra by application of the Log Log function. If the surface is fractal the Log Log graph should be highly linear, with at negative slope (see, e.g., Fractal Surfaces, John C. Russ, Springer-Verlag New York, LLC, July, 2008).

Example 3

An array of microneedles including a nanopatterned surface was formed. Initially, an array of microneedles as illustrated in FIG. 2 was formed on a silicon wafer via a photolithography process. Each needle included two oppositely placed side channels, aligned with one through-die hole in the base of the needle (not visible on FIG. 2).

Microneedles were formed according to a typical micro-machining process on a silicon based wafer. The wafers were layered with resist and/or oxide layers followed by selective etching (oxide etching, DRIE etching, iso etching), resist stripping, oxide stripping, and lithography techniques (e.g., iso lithography, hole lithography, slit lithography) according to standard methods to form the array of microneedles.

Following formation of the microneedle array, a 5 µm polypropylene film including a DN2 pattern formed thereon as described above in Example 1, the characteristics of which are described at sample 2 in Table 4, was laid over the microneedle array. The wafer/film structure was held on a heated vacuum box (3 inches H₂O vacuum) at elevated temperature (130° C.) for a period of one hour to gently pull the film over the surface of the microneedles while maintaining the nanopatterned surface of the film.

FIGS. 34A-34D illustrate the film over the top of the array of microneedles, at increasing magnifications.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A device for delivery of a bioactive agent across a dermal barrier, the device comprising:

a microneedle and a plurality of nanostructures fabricated on a surface of the microneedle, the nanostructures being arranged in a predetermined pattern, wherein at least a portion of the nanostructures have a cross-sectional dimension of less than about 500 nanometers and greater than about 5 nanometers and an aspect ratio of from about 0.2 to about 5, wherein the microneedle further contains a channel; and a reservoir that is in fluid communication with the channel of the microneedle and that contains a composition having a viscosity of greater than about 5 centipoise and comprising a bioactive agent.

2. The device according to claim 1, wherein the composition includes the bioactive agent in a concentration of greater than about 5 mg/mL.

3. The device according to claim 1, wherein the bioactive agent has a molecular weight of greater than about 100 kDa.

4. The device according to claim 1, wherein the bioactive agent is a protein therapeutic.

5. The device according to claim 1, the composition further comprising one or more pharmaceutically acceptable excipients.

6. The device according to claim 5, wherein the pharmaceutically acceptably excipient comprises a solvent, a penetration enhancer, a thickening agent, a wetting agent, a lubricant, or an emollient.

7. The device according to claim 1, wherein the pattern further includes microstructures, wherein the nanostructures have a cross-sectional dimension smaller than the microstructures.

8. The device according to claim 7, wherein the microstructures have a cross-sectional dimension of greater than about 500 nanometers and the nanostructures have a cross-sectional dimension of less than about 300 nanometers.

9. The device according to claim 7, further comprising second nanostructures having a cross-sectional dimension less than the cross-sectional dimension of the microstructures and greater than the cross-sectional dimension of the plurality of nanostructures.

10. The device according to claim 7, wherein at least a portion of the microstructures have a cross-sectional dimension of greater than about 500 nanometers and less than about 10 micrometers.

11. The device according to claim 7, wherein at least a portion of the nanostructures have a cross-sectional dimension of from about 20 to about 400 nanometers and at least a portion of the microstructures have a cross-sectional dimension of from about 600 nanometers to about 1.5 micrometers.

12. The device according to claim 7, where at least a portion of the microstructures have a height of from about 20 nanometers to about 1 micrometer.

13. The device according to claim 7, wherein at least a portion of the microstructures have an aspect ratio of from about 0.2 to about 5.

14. The device according to claim 7, wherein the cross-sectional dimension of the microstructures is greater than the height of the microstructures.

15. The device according to claim 14, wherein at least a portion of the microstructures have an aspect ratio of from about 0.15 to 1.

16. The device according to claim 7, wherein at least a portion of the nanostructures have a height greater than a cross-sectional dimension.

17. The device according to claim 1, wherein at least a portion of the nanostructures have a center-to-center spacing of from about 50 nanometers to about 1 micrometer.

18. The device according to claim 1, wherein the pattern has a fractal dimension of greater than about 1.

19. The device according to claim 1, wherein the microneedle surface containing the plurality of nanostructures has an average surface roughness between about 10 nanometers and about 200 nanometers.

20. The device according to claim 1, wherein the composition has a viscosity of from about 10 centipoise to about 50 centipoise.

21. The device according to claim 1, wherein the composition includes the bioactive agent in a concentration of from about 35 mg/mL to about 500 mg/mL.

22. The device of claim 1, wherein at least a portion of the nanostructures have a height of from about 10 nanometers to about 1 micrometer.

23. The device of claim 1, wherein at least a portion of the nanostructures have an aspect ratio of from about 0.5 to about 3.5.

24. The device according to claim 1, wherein the microneedle surface containing the plurality of nanostructures has an effective shear modulus between about 4 MPa and about 320 MPa.

25. The device according to claim 1, wherein at least a portion of the nanostructures have a cross-sectional dimension of from about 100 to about 300 nanometers.

26. The device according to claim 1, wherein the nanostructures have approximately the same cross-sectional dimension.

27. The device according to claim 26, wherein the channel has a length of from about 10 to about 800 micrometers.

28. The device according to claim 1, wherein the ratio of the cross sectional dimension of two adjacent nanostructures to the center-to-center spacing between those two structures is between about 1:1 and about 1:4.

29. The device according to claim 1, wherein at least a portion of the nanostructures have an equidistant spacing.

30. The device according to claim 1, wherein at least a portion of the nanostructures are in the form of pillars.

31. The device according to claim 1, wherein the channel has a cross-sectional dimension of from about 1 to about 100 micrometers.

32. The device according to claim 1, wherein the device contains a microneedle array that contains the microneedle.

33. The device according to claim 32, wherein the array contains a base having an aperture, wherein the aperture is in at least partial alignment with the channel of the microneedle.

34. The device according to claim 33, wherein the reservoir is attached to a substrate upon which the array is located.

35. The device according to claim 33, wherein the reservoir is removably connected to the array.

36. A method for delivering a bioactive agent to a subject comprising:
penetrating the stratum corneum of the subject with a microneedle, the microneedle comprising a plurality of nanostructures fabricated on a surface of the microneedle, the nanostructures being arranged in a predetermined pattern, wherein at least a portion of the nanostructures have a cross-sectional dimension of less than about 500 nanometers and greater than about 5 nanometers and an aspect ratio of from about 0.2 to about 5; and
transporting a composition through the microneedle at a rate of greater than about 0.4 mg/hr/cm$^2$ based upon the surface area of the microneedle.

37. The method according to claim 36, wherein the stratum corneum is a layer of the subject's skin, the skin including tight junctions between cells of the skin, the nanostructures rearranging tight junctions between the cells, thereby increasing porosity of the skin.

38. The method according to claim 37, wherein the rearrangement of the tight junctions leads to an increase in the porosity of a second tissue type that is not in contact with the microneedle.

39. The method according to claim 38, wherein the second tissue type is vascular tissue.

40. The method according to claim 38, wherein the second tissue type is vascular tissue.

41. The method according to claim 36, wherein the composition has a viscosity of greater than about 5 centipoise.

* * * * *